US011051769B2

(12) United States Patent
Brunicardi

(10) Patent No.: US 11,051,769 B2
(45) Date of Patent: Jul. 6, 2021

(54) HIGH DEFINITION, COLOR IMAGES, ANIMATIONS, AND VIDEOS FOR DIAGNOSTIC AND PERSONAL IMAGING APPLICATIONS

(71) Applicant: THE REGENTS OF THE UNIVERSITY OF CALIFORNIA, Oakland, CA (US)

(72) Inventor: F. Charles Brunicardi, Pacific Palisades, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 55 days.

(21) Appl. No.: 16/140,274

(22) Filed: Sep. 24, 2018

(65) Prior Publication Data
US 2019/0090824 A1    Mar. 28, 2019

Related U.S. Application Data

(63) Continuation of application No. PCT/US2017/023669, filed on Mar. 22, 2017.
(Continued)

(51) Int. Cl.
*A61B 6/03* (2006.01)
*A61B 5/055* (2006.01)
(Continued)

(52) U.S. Cl.
CPC .............. *A61B 6/032* (2013.01); *A61B 5/055* (2013.01); *A61B 5/742* (2013.01); *A61B 6/466* (2013.01);
(Continued)

(58) Field of Classification Search
None
See application file for complete search history.

(56) References Cited

U.S. PATENT DOCUMENTS 6,233,480 B1    5/2001    Hochman
6,359,618 B1    3/2002    Heirich
(Continued)

FOREIGN PATENT DOCUMENTS

EP    0758477    2/1997
EP    1406215 A1    4/2004
(Continued)

OTHER PUBLICATIONS

Agile Software Development & Business IT Consulting, "Computer Animations for the Healthcare, Pharmaceutical and Medical Education sectors", company publication Feb. 2012, 5 pages, downloaded from https://web.archive.org/web/20120308154016/http://www.a115.bg/medical_animations.html on Sep. 24, 2018.
(Continued)

*Primary Examiner* — Nancy Bitar
(74) *Attorney, Agent, or Firm* — O'Banion & Ritchey LLP; John P. O'Banion

(57) ABSTRACT

High definition, color images, animations, and videos for diagnostic and personal imaging applications are described along with methods, devices and systems for creating the images, as well as applications for using the images, animations and videos.

24 Claims, 14 Drawing Sheets

Related U.S. Application Data

(60) Provisional application No. 62/313,530, filed on Mar. 25, 2016.

(51) Int. Cl.

| | |
|---|---|
| A61B 6/00 | (2006.01) |
| A61B 8/00 | (2006.01) |
| G06T 11/00 | (2006.01) |
| G06T 15/06 | (2011.01) |
| G06T 15/50 | (2011.01) |
| A61B 8/08 | (2006.01) |
| G16H 50/50 | (2018.01) |
| G06T 15/04 | (2011.01) |
| G09B 23/28 | (2006.01) |
| A61B 5/00 | (2006.01) |

(52) U.S. Cl.
CPC .......... *A61B 6/5211* (2013.01); *A61B 6/5247* (2013.01); *A61B 8/463* (2013.01); *A61B 8/466* (2013.01); *A61B 8/483* (2013.01); *A61B 8/523* (2013.01); *A61B 8/5215* (2013.01); *A61B 8/5261* (2013.01); *G06T 11/001* (2013.01); *G06T 15/04* (2013.01); *G06T 15/06* (2013.01); *G06T 15/506* (2013.01); *G09B 23/28* (2013.01); *G16H 50/50* (2018.01); *A61B 6/481* (2013.01); *A61B 8/481* (2013.01); *A61B 2576/00* (2013.01)

(56) References Cited

U.S. PATENT DOCUMENTS

| | | | |
|---|---|---|---|
| 8,469,713 B2 | 6/2013 | Kron | |
| 8,494,250 B2 | 7/2013 | McDermott | |
| 8,674,989 B1 | 3/2014 | Dalal | |
| 10,867,453 B2* | 12/2020 | Chen | G06T 7/564 |
| 2003/0023156 A1 | 1/2003 | Pappas | |
| 2004/0259057 A1 | 12/2004 | Kim | |
| 2007/0070063 A1 | 3/2007 | Sumanaweera | |
| 2008/0134094 A1 | 6/2008 | Samadani | |
| 2009/0184955 A1 | 7/2009 | Thiele | |
| 2009/0191529 A1 | 7/2009 | Mozingo | |
| 2010/0157018 A1 | 6/2010 | Lampotang | |
| 2011/0125016 A1 | 5/2011 | Lazebnik | |
| 2013/0278600 A1* | 10/2013 | Christensen | G06T 19/20 345/420 |
| 2016/0045317 A1* | 2/2016 | Lang | G05B 19/4099 700/98 |
| 2019/0371080 A1* | 12/2019 | Sminchisescu | G06T 19/00 |

FOREIGN PATENT DOCUMENTS

| | | |
|---|---|---|
| EP | 1683485 | 7/2006 |
| WO | 2001064106 | 9/2001 |
| WO | 2009004296 A1 | 1/2009 |
| WO | 2014145267 A1 | 9/2014 |
| WO | 2014159082 A1 | 10/2014 |

OTHER PUBLICATIONS

ISA/US, United States Patent and Trademark Office (USPTO), International Search Report and Written Opinion dated Jul. 21, 2017, related PCT international application No. PCT/US2017/023669, pp. 1-16, claims searched, pp. 16-23.

BCC Research, "Global Markets for CT Scanners", HLC024A, Oct. 2012, ISBN: 0-89336-128-3, 211 pages.

BCC Research, "Global Markets for Medical Imaging Reagents and Analysis Equipment", HLD040D, Jan. 2013, ISBN: 0-89336-317-0, 226 pages.

BCC Research, "Medical Magnetic Resonance Imaging (MRI): Technologies and Global Markets", HLC078B, Sep. 2013, ISBN: 1-56965-548-0, 156 pages.

Boppart, Stephen A. et al., "Optical probes and techniques for molecular contrast enhancement in coherence imaging", Journal of Biomedical Optics 10(4), 041208 (Jul./Aug. 2005), 041208-1 to 041208-14.

BCC Research, "Medical Ultrasound Devices: Technologies and Global Markets", IAS040A, Jan. 2013, ISBN: 0-89336-242-5, 120 pages.

* cited by examiner

HIGH DEFINITION, COLOR IMAGES, ANIMATIONS, AND VIDEOS FOR DIAGNOSTIC AND PERSONAL IMAGING APPLICATIONS

CROSS-REFERENCE TO RELATED APPLICATIONS

This application is a 35 U.S.C. § 111(a) continuation of PCT international application number PCT/US2017/023669 filed on Mar. 22, 2017, incorporated herein by reference in its entirety, which claims priority to, and the benefit of, U.S. provisional patent application Ser. No. 62/313,530 filed on Mar. 25, 2016, incorporated herein by reference in its entirety. Priority is claimed to each of the foregoing applications.

The above-referenced PCT international application was published as PCT International Publication No. WO 2017/165566 on Sep. 28, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Appendix A referenced herein is a computer program listing in a text file entitled "UC-2014-144-4-LA-US-computer-program-listing.txt" created on Sep. 24, 2018 and having a 129 kb file size. The computer program code, which exceeds 300 lines, is submitted as a computer program listing appendix through EFS-Web and is incorporated herein by reference in its entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to imaging modalities used in healthcare, and more particularly to a transformational imaging and simulation platform that extends photo-realism to healthcare and other uses.

2. Background Discussion

The primary purpose of most medical imaging modalities is to help physicians of all specialties, as well as patients, provide accurate diagnoses to improve therapeutics. The beginning of modern imaging began with William Rontgen and the discovery of x-rays in 1895. The advent of CT scanning, MRI scanning, Ultrasound, PET scanning and other computer generated imaging has provided a remarkable advance in healthcare worldwide over the last thirty years that greatly enhanced the ability of healthcare providers to diagnose and treat diseases of all types, as well as avoid unnecessary and costly procedures, such as exploratory laparotomies.

While these advances are laudable, the quality of the images for almost all imaging modalities produced is still remarkably primitive. The images being produced in healthcare are currently presented in primitive black and white images and are difficult to interpret except by few highly trained specialists, such radiologists, nuclear medicine specialists and imaging technicians. There are attempts using relatively primitive color schemes in low definition and in 3-D. Additionally, low definition animations of surgeries and other procedures, such as those made by DaVinci Robot or Simbionix, do exist and have been demonstrated to have limited training value for surgical trainees. There are medical video games with low definition, unrealistic animations, such as Atlus' Trauma Center Series, however these games are not practical for medical and surgical training purposes.

Recent advancements have been made in technologies relating to photo-real render engines, which primarily depend on the use of shader code applied to an isometric surface model. Generally, CT scans are volumetric and are designed for clinical viewing only. While converting volumes to isometric surfaces is possible with existing 3rd party applications, the converted surface lacks detail with respect to information about the physical properties of the materials relating to the visible wavelength—color, glossiness, etc.

Raw scan data from current imaging modalities also isn't high resolution due to limitations with the current generation of scanners. Additionally, the raw data can be very noisy with lots of artifacts that will be in direct conflict with generating photo-real rendering. Most scans are just done to the localize area of interest, so getting a full body scan to build isn't practical.

Current technology would require a 3rd party company to process the scan data and manually make a photo-real rendering of it, which would be cost prohibitive and overly time consuming (e.g. weeks of time to produce).

Furthermore, some scanners use custom file formats that only work with their software, making it hard to process to the data to make a photo-real rendering.

Even with the current advances in MRI and CT scanners, the data is presented in a purely clinical manner, which can be very confusing and intimating to even the trained eye, but to the patient it's even more overwhelming.

Accordingly, creating a new tool that can alleviate these issues and provide doctors, surgeons, radiologists, teachers, and patients a new means to view the data is vitally important.

BRIEF SUMMARY

One aspect of the present disclosure is a transformational imaging and simulation platform, herein referred to as "SIMaging."

Another aspect is systems and methods to convert a conventional two dimensional black and white medical image into a colorized "photorealistic" image, and automatically render diagnostic information based on the photorealistic image.

Actual photorealism, color images of the patient's body, organs, tissues and cells transforms diagnostic capability for the radiologist and healthcare providers of all specialties, as well as education of future healthcare providers and the patients themselves. In turn, these personalized images may be used for real time simulations coupled with artificial intelligence that may be used for practice of any intervention/operation, as well as realtime use during virtually any medical procedure to guide surgeons and interventionalists of all specialties, including all surgical specialties, gastroenterology, radiology, pulmonary, anesthesia, pain medicine, cardiology, etc, through the procedures.

The images and simulations produced from the present technology may be used on a daily basis to transform imaging, diagnostic capabilities and therapy in all hospitals, centers, clinics and medical schools worldwide. The system may also be connected to artificial intelligence to guide the surgeon/interventionalist through procedures, like a GPS system, in real time, while documenting each step of the procedure according to standard operating protocols, thus standardizing and documenting procedures and entering the information into databases in realtime. The images and simulations can be used on a daily basis to transform the education of surgeons and interventionalists of all specialties and their trainees in all medical universities and hospitals and clinics worldwide. These advances improve quality of care, improve documentation and lower costs of complications, readmissions and documentation.

The personalized images produced from the technology can also be used for home health systems that would help patients monitor such data as their weight, body mass, body fat content, body water content, body muscle content, which can be connected to an electronic medical record to assist in health maintenance, as well as to track response to therapy and recovery from operations over time. Users visualize and save images of their body images over time. Expecting women (and their partners) may visualize photorealistic images of their babies in utero. The personalized images, coupled with artificial intelligence, help guide personal grooming, make-up applications and dress for all different types of events. The personalized images and simulations may also be used for entertainment purposes for the movie, television, internet, and gaming industries. The platform may further be used to evaluate employees before and during employment, for example, athletes, on a global basis.

In one implementation, the technology of the present description is incorporated into imaging machines for hospitals, clinics, operating rooms, interventional suites and medical schools and laboratories, worldwide. Further embodiments include systems comprising home health units using computer gaming systems such as Kinnect, Wii, Oculus Rift, and Playstation to assist in home health as well as personal grooming and gaming using computer and robotic avatars. The technology of the present description may also be used for movie, television, music videos and internet. In doing so, this would represent the next generation in personalized imaging and therapy to enhance healthcare, education and entertainment on a global scale.

Another aspect of the technology described herein is to combine the photorealism imaging technology with enhanced molecular contract technology. The ability to produce photorealism imaging, in high definition, with enhanced molecular contrast, and the production of personalized animated simulations from these images represents the benchmark transformation of personalized medicine and surgery on a global scale. Therefore, the use of SIMaging represents a transformation in health maintenance and healthcare delivery that will revolutionize the quality of life and longevity of mankind, as we enter into the age of personalized medicine and surgery.

Another aspect of the technology described herein is the use of tissue specific gene delivery-imaging platform to enhance the imaging differences between healthy tissues and cells, and diseased tissues and cells, using state-of-the-art "molecular contrast agents." In doing so, personalized photorealism renderings and simulations of the healthy and diseased body, organs, tissues and cells can be produced to assist both health care providers of all specialties and humans worldwide to evaluate their overall body health, diagnose their diseases of all types, practice, plan and assist in operations and therapeutic interventions in unlimited applications, as well as help track recovery from therapies, operations and interventions.

The photorealism images produced by the technology can be used for real time personalized animated simulations that will assist surgeons and other interventionalists of all specialties to improve their quality of care for their patients. These personalized animated simulations of both healthy and diseased organs, tissues and cells will assist health care providers of all specialties worldwide to evaluate their patients overall body health and diagnose their diseases of all types. The personalized animated simulations will also enable surgeons and other medical practitioners of all specialties to practice and plan their proposed procedures on their patients' images before the operation or procedure. Furthermore, the personalized animated simulations coupled with artificial intelligence and robotic assistance can be used during the procedure using specialized glasses or computer screens to assist surgeons and interventionalists with the procedures in real time to improve quality of care, reduce complications and reduce costs of healthcare by guiding the surgeon and interventionalist using standard-of-care protocols while capturing the details of the operation or intervention in real time and into electronic healthcare databases. The personalized animated simulations and artificial intelligence with robotic assistance will assist in standardization and documentation of all procedures in real time. In doing so, the quality of care and quality of life for the patients, as well as quality of life for the healthcare providers, may greatly improved, while significantly lowering healthcare costs.

The personalized animated simulations can also be used for educational purposes for health care providers, future healthcare providers and patients. The personalized animated simulations may be used in home health systems to help patients evaluate their own health status, as well as disease states and recovery from therapies, operations and other interventions.

The SIMaging technology can also be extended to entertainment purposes, such as movies, television, music videos and internet computer gaming of all types, as well as to personal grooming applications and simulated aging by using computer and robotic avatars. The technology can be used by private industry to evaluate employee health status before and during employment, such as the sports industry worldwide. The technology can also be used for farming husbandry purposes. Furthermore, the technology can be used for research purposes in clinics and laboratories worldwide. Simulated procedures can be carried out and meaningful predictions can be made prior to use of lab animals or appropriate human participants.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

A. SIMaging System and Method Overview

The technology described herein is directed to transformational imaging and simulation platforms, "SIMaging," applied to current medical imaging modalities to greatly enhance the accuracy and interpretability of medical images. The technology facilitates accurate diagnoses, improved therapeutics, and enhanced training for healthcare professionals, patients and others.

SIMaging provides novel methods to present medical CT/MRI scans (and other acquired data sets such as X-ray, photos, etc.) to patients and doctors, allowing them to see in a very easy to decipher photorealistic real-time rendering presentation by creating new geometry.

SIMaging is based largely on development of a "SIM-SET," which is a parametrically built representation of the human body, or portion of a human body, with fully photo-real geometry and shaders that can be rendered in real-time. The SIM-SET is automatically aligned and calibrated to one or more sources of input data such as: MRI/CAT scans, weight, BMI, height, x-rays, photos, manual input, etc. This dynamically creates a 3D patient SIM-SET to an almost exact representation of the real patient with all of the pre-defined photo-real characteristics built into it for generating imagery with realistic looking skin, bone, and flesh using a data base of BRDF (bidirectional reflectance distribution function) shaders with subsurface scattering.

Figure 1:
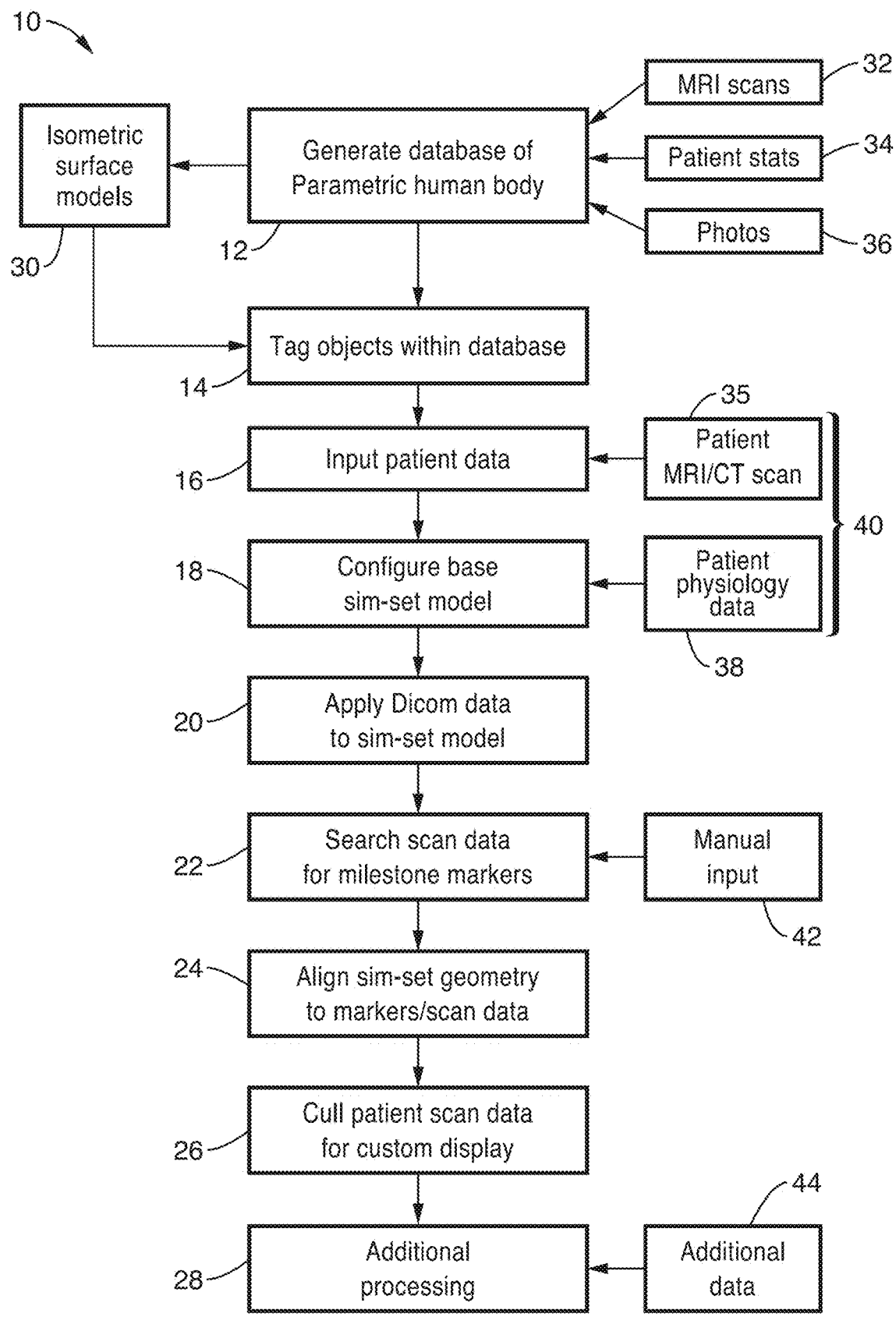
FIG. 1 is a schematic flow diagram of a method for generating a parametric simulated model (SIM-SET) of an anatomical region of a patient in accordance with the present description.

FIG. 1 shows a schematic flow diagram of a method 10 for generating a parametric simulated model (SIM-SET) of an anatomical region of a patient in accordance with the present description. First, a database of a parametric human body (SIM-SET), or anatomical portion of the body, is created at step 12 by acquiring input data in the form of one or more of imaging scans 32 (e.g. MRI/CT/US scans), patient statistics 34, photos 36, etc. The SIM-SET comprises mainly of volume data and/or isometric surface models 30 of one or more aspects of the anatomy (e.g., for both male and female patients), the surface models 30 being designed for photo-real real-time VR rendering.

Next at step 14, each object in the SIM-SET is 'tagged.' The tagged data is configured so that any piece of the human parametric model can be turned on or off for viewing (e.g. to show skeletal, or vascular and muscle together, etc).

The data from steps 12 and 14 may be stored in a secure dedicated database, piggy back onto existing hospital systems, or may be completely integrated into a manufacture's database (such as the scanner manufacturer, GE, or the like).

With the database established, the system (see, e.g., system 100 shown in FIG. 2) is ready to be applied to individual patients. At step 16, individual patient data is input, which may be in the form of an MRI/CT scan 35, or the like.

At step 18, a patient specific, base SIM-SET model is developed from the database as a function of input patient physiology data 38, e.g. specific physical characteristics of the patient. Both the patient scan 35 and physiology data 38 are patient data 40 that is specific to the individual patient.

At step 20, DICOM data/files (preferably non-proprietary) are extracted from a CT/MRI scanners.

At step 22 the scan data is searched for specific milestone markers of anatomy that will later be used to align the SIM-SET geometry. Manual input 42 may be used for selecting one or more milestone markers if a patient has a unique anatomy, e.g. birth defects, amputations, or other abnormalities.

At step 24 the markers are then used to perform isometric surface alignment of the SIM-SET geometry to the patient's scan 35. In a preferred embodiment, the alignment is done taking into account other input data 38 such as weight, height, BMI, X-ray, photos, etc. This alignment is performed on both volume data and surfaces, and can also be adjusted by manual input 42 via selecting the key structures on different slices of a MRI/CT scan to help fine-tune the SIM-SET.

Using the tags from the SIM-SET, the patient scan data 35 can now be 'culled' at step 26 for rendering and custom display via a fully controlled viewing system for showing all the data in a photo-real presentation.

Additional processing may be performed at step 28 as a function of further input 44. For example, photographic reference of skin color can be input to make the exact tone and hue of the patient. Now that that a fully 3D model of the patient's body exists, other data can now be connected to it, e.g. auto-alignment and projection of wound, surgeon mark-ups, or even X-rays (for example) directly onto the surface of the body, essentially generating a 3D photo gallery based on body location. Notes and other text files can also be connected to different locations on the body, giving the patient and the doctor a fully 3D representation of data.

Figure 2:
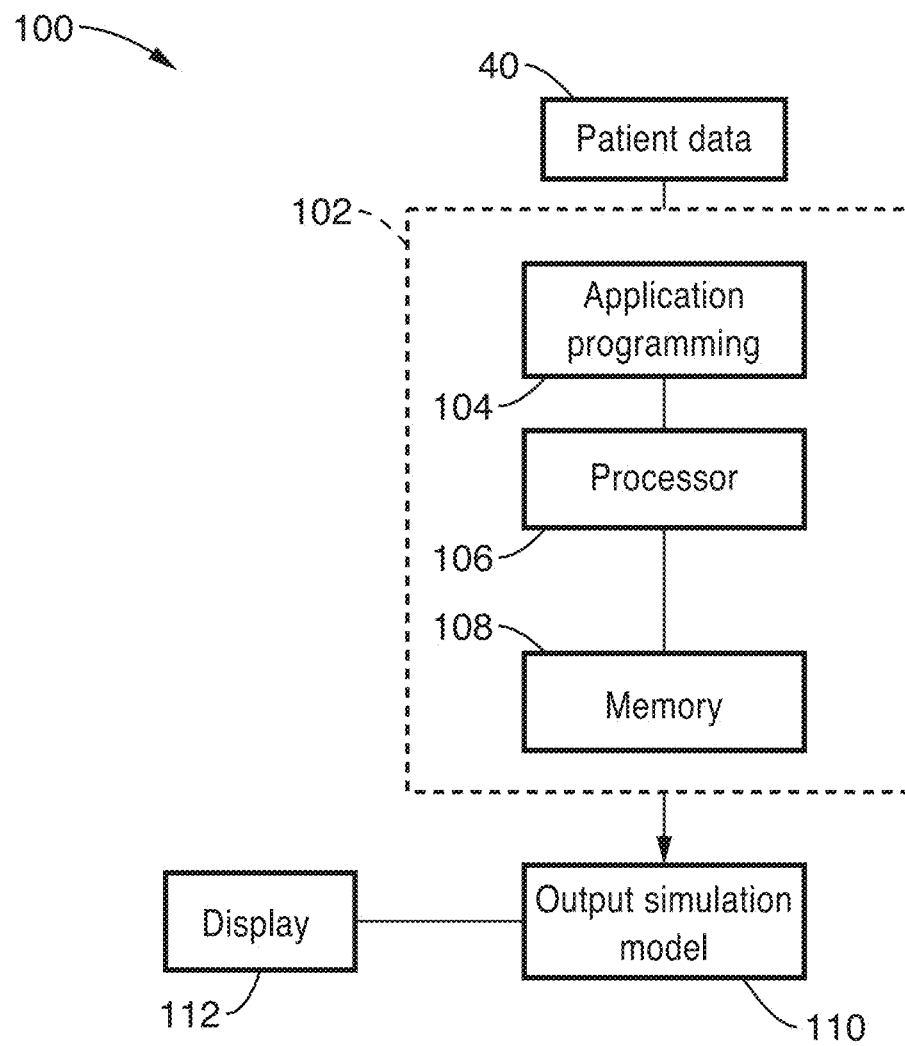
FIG. 2 is a system for outputting the SIM-SET of FIG. 1 based on input patient data.

Referring to the system 100 shown in FIG. 2 the output SIM-SET or simulation model may be rendered in real-time for view on a display 112. System 100 further comprises a computer/server 102 comprising a processor 106 and memory 108 for storing application programming 102. Wherein programming 102 comprises instructions configured for execution by the processor for transforming the input patient data 40 according to method 10 into the output simulation model 110 for display or with VR assisted headgear (not shown).

Programming 110 is furthermore adaptable so that doctors and patients can add data to the SIM-SET over time. For example, additional scans 35 can be added at a later date to show progress over time, or a patient could take photos of a post-op condition and apply them to the model data set. Tracking a patient's weight loss may also be represented in an animated time-lapse photo-real presentation.

Because the data SIM-SET has anatomy information that is not present in the patient scans (it can extrapolate the entire body based off of just a chest CT scan and some other input data, for example), it may also serve as an educational reference for the entire body, and can be viewed and explored as such. Hence the name "Photo-real Simulation-Visualography" because of the extrapolation of un-scanned portions of the body.

Because the clinical scan data 35 is still maintained in the SIM-SET, it can be viewed at the same time if needed. This allows the physician to show raw data to a patient in combination with photo-real rendering.

Furthermore, because lighting and reflections are integral to photo-real rendering, any photo-real HRDI (high range dynamic image) environments can be selected for viewing the SIM-SET within, such as: a generic modern doctors office, abstract white cyc, park setting, etc. Several environment presets can be included and used depending on the desired presentation of the SIM-SET.

The SIMaging systems and methods of the present description may be integrated into the medical field via several different avenues, such as working directly with manufactures to include it with their MRI/CT scanners, or to have it be a stand-alone 3rd party application that patients or doctors can use from home or at school.

The SIMaging systems and methods of the present description is capable of producing color high definition photographs (photorealism) and animated simulations of any person's body, organs, tissues and cells from the images obtained from standard imaging modalities, such as CT scans, MRI, ultrasound, PET scans, brain scans, nuclear medicine scans, optical imaging scans, and other targeted imaging technology, using high definition animation platforms.

SIMaging systems and methods of the present description may be expanded to be the foundation for visualizing not just scan data (MRI, CT, etc.), but any other input data that benefits from alignment with a 3D photo-real representation of the patient, such as: pre-surgery markup photos, post-surgery follow up photos, X-rays, artificial joints, pace makers, etc.

This photo real virtual patient may be used to show the results of a recent scan or surgery, or may be used with VR assisted viewing for a surgeon performing an evasive procedure, or finally to a teacher showing students a photo-real anatomy lesson. And as additional data sets are collected over the years, it can also provide a fully visual historical presentation of a patient to better track their health and progress.

The technology of this disclosure can be described in terms of several main embodiments, which will now be described. In one embodiment, referred to herein as Embodiment 1, conventional images from standard diagnostic imaging platforms (e.g., DICOM format) are transformed into high definition colorized, "photorealistic" images using the SIMaging system and method of the present description.

In another embodiment, referred to herein as Embodiment 2, three dimensional animations are created from the photorealistic images.

In another embodiment, referred to herein as Embodiment 3, the photorealistic images are rendered in such a way as to depict medical conditions of interest. For example, an image of tissue or an organ would visually depict cancerous areas in the tissue or organ.

It will be appreciated that the technology described herein includes other embodiments as described herein and as would be appreciated to those skilled in the art in view of the description herein.

B. General Embodiment 1

In General Embodiment 1, conventional images from standard diagnostic imaging platforms (e.g., DICOM format) are transformed into high definition colorized, "photorealistic" images using the systems and methods detailed above.

For example, animated platforms of both cartoon as well as photorealism movies may be generated using computer generated imaging facial recognition technology to enhance the standard diagnostic images that are produced by the different imaging modalities. Preferably this system would be implemented in close collaboration between the surgeons, interventionalists of all procedures, radiologists, animators and software developers to combine the use of medical knowledge of the human body, both anatomy and physiology, and therapeutic interventions with computer animation platforms to produce photorealism images and simulations that are created for the benefit of healthcare.

For example, a CT/MRI/US scan of a patient's breast and/or internal gastrointestinal organs may be input as scan 35 (see FIG. 1) or patient data 40 (FIG. 2) into system 100 and is transformed into output simulation model 110, e.g. as high definition colorized, "photorealistic" images or animations in collaboration with, for example, surgeons and other interventionalists who can interpret the images and their relevance to health and disease. This may be performed for both normal and healthy tissues versus those tissues that are diseased. Normal and healthy breast or appendix images may be used for the initial images to create a photograph of the breast or appendix similar to that seen during an operation. Once the normal breast or appendix is visualized, different phases of the diseased breast or inflamed appendix can be animated using input CT scans, MRI scans, and ultrasounds of patient's breast or inflamed appendices, which are correlated with the images seen in the operating room during open operations, as well as laparoscopic appendectomies. The same can be applied for gallbladders that are both normal as well as inflamed. For both breast or appendix, the still or animated images could progress to cancer of the breast or perforated appendix with surrounding purulent material. Once the fundamentals are developed for these organs, the technology can then be applied to any disease process that can be imaged such as cardiovascular diseases, cancer, arthritis, chronic inflammatory diseases, and any range of normal tissues versus pathologic states that can be imaged.

In another example, CT/MRI/US scans of the body are performed on a patient. The information for each organ seen on the primitive images of the CT/MRI/US is evaluated and compared with known images and photographs of the human body and organs from anatomy atlases and other documented sources. Using, for example, the expertise of a surgeon or other interventionalist, or information in a database of related information previously developed, the images of the organs on the CT/MRI/US scan of the patient's body are transformed into a high definition, photorealistic rendering of the internal gastrointestinal organs using the system and methods of the present description. Initially, the program can be focused on one organ, such as the liver or appendix, to simplify the process. Cross-references of the animation being produced with the CT scan may be done on a continuous basis to ensure accuracy of the photo being produced. Once completed, the CT/MRI/US scan may be reviewed and compared with the photorealism rendering of the rendered animation image. A determination may be made of whether the system is able to reproduce the photorealism images from the DICOM format CT/MRI/US scan without the assistance of the animators and surgeon. Once this is accomplished, a database of all internal organs is developed and tested against CT/MRI/US scans from multiple patients. This process may be repeated for other imaging modalities of known patients, such as PET-CT and nuclear medicine scans.

Simultaneously, the same patient's head and body may be scanned into the animation computer system using a 4 camera scanning facial recognition technology such as that provided by Hydraulx, Inc. The CT/MRI/US scan may be reviewed in collaboration with the surgeon, radiologist and the animation team and the information then transferred into the system (e.g. using NECTAR and Dell computers animation software, such as Poser Pro 2010 3D Modeling & Animation). The information of each organ seen on the primitive images of the CT/MRI/US may be discussed in detail and compared with known images and photographs of the human body and organs from anatomy atlases and detailed information obtained from other documented sources. With the guidance of the surgeon, the images of the organs on the CT/MRI/US scan of the patient's body are then transformed into a high definition photorealism rendering of the internal gastrointestinal organs using the system. As before, there may be a focus on one organ, such as the liver or appendix, to simplify the process. Cross-references of the animation being produced with the CT/MRI/US scan may be done on a continuous basis to ensure accuracy of the photo being produced. Once completed, the image of the CT/MRI/US scan will be reviewed and compared with the photorealism rendering. A determination may be made of whether the system is able to reproduce the photorealism images from the DICOM format CT/MRI/US scan without the assistance of the animators and surgeon. Once this is accomplished, the database of all internal organs may be developed and tested against other patients' CT/MRI/US scans. This process will be repeated for other imaging modalities of known patients, such as PET-CT and nuclear medicine scans.

It will be appreciated, therefore, that an aspect of the technology described herein is to create high definition colorized animated images that are accomplished by collaboration of the system of the present description with diagnostic imaging platforms from CT scans, MRI, ultrasound, mammography, brain scans, nuclear medicine scans, PET scans to enhance diagnostic capability and therapy for healthcare providers and education of patients.

Figure 3A:
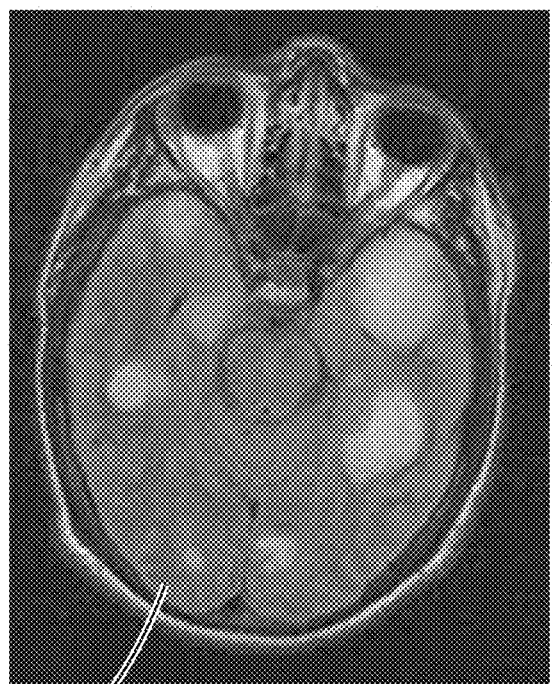
FIG. 3A and FIG. 3B illustrate enhancing an MRI of the brain according to an embodiment of the technology described herein.
Figure 3B:
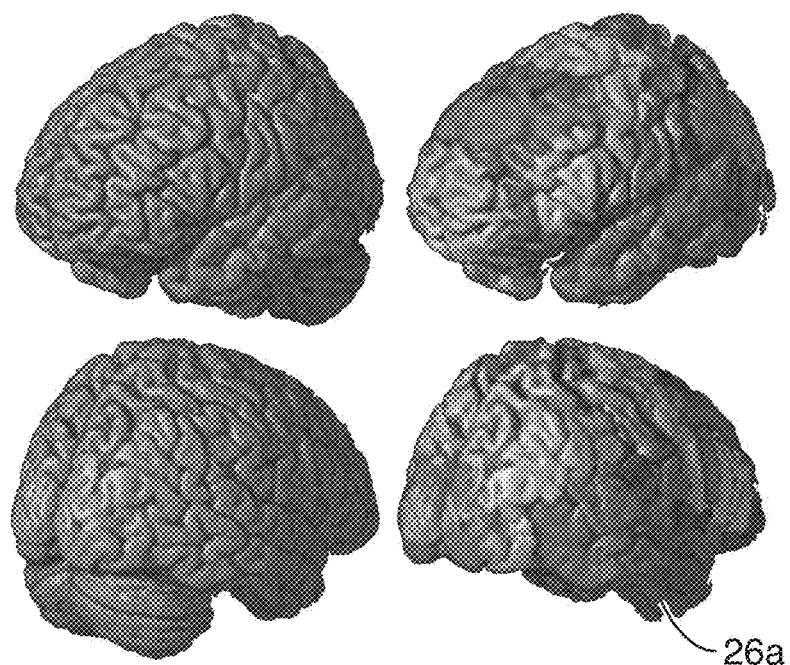

In one exemplary configuration, FIG. 3A and FIG. 3B illustrate enhancing an MRI of the brain according to an embodiment of the present technology. An MRI scan 40a is input into the system 100 to generate and output one or more photorealistic simulations 26a of the brain.

Figure 4A:
FIG. 4A and FIG. 4B illustrate enhancing an angiogram of an aortic aneuryism with an endovascular stent according to an embodiment of the technology described herein.
Figure 4B:
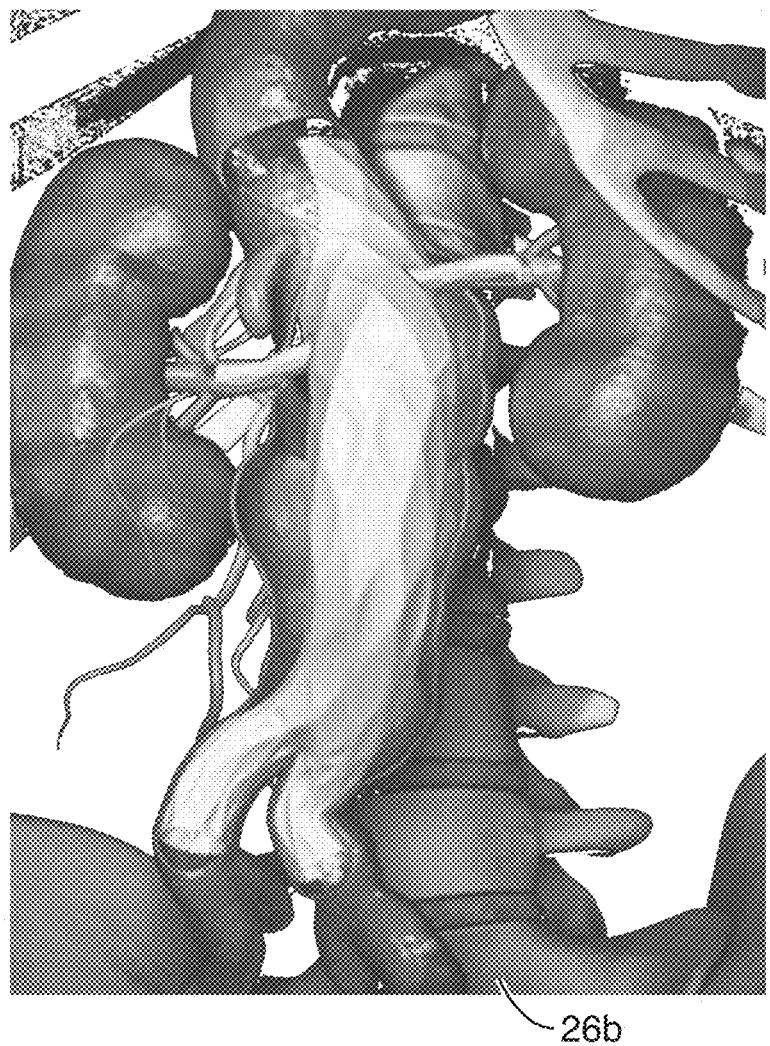

FIG. 4A and FIG. 4B illustrate another exemplary embodiment for enhancing an angiogram of an aortic aneuryism with an endovascular stent according to an embodiment of the technology. In such embodiment, angiogram 40b is input into the system 100 to generated and output photorealistic simulation 26b of the stent and surrounding anatomy in the chest cavity.

Another exemplary embodiment may entail inputting a standard image of fetal ultrasound to generate a photorealism rendering of the baby within the mother's womb in utero. A further exemplary embodiment may include inputting a standard image of a breast seen on mammogram and/or MRI scan to generate an animated image of the breast, or inputting a standard image of liver cancer seen on CT scan to generate photorealism images of liver cancer metastases.

It will also be appreciated that potential levels of images and generated simulation/animation are as follows: 1) whole body, face and skull, 2) organs, 3) cells, 4) molecular pathways and functional genomics, 5) atomic and 6) subatomic.

C. General Embodiment 2

In this embodiment, animated simulations are generated from the personalized images. The result can be used for medical and surgical simulation video games for training of interventionalists of all specialties. Animated simulation for any interventional procedures would help practitioners of all specialties practice prior to the actual procedure and also help guide the practitioner in real time through the procedure using artificial intelligence to track milestones of the procedure, as well as track the progress of the milestones for the procedure in real time in the medical records. This would lead to standardization of procedures on a global scale and improve outcomes and quality of care. In addition, practitioners would also avoid the need for costly and often inaccurate dictations thus improving documentation of healthcare.

System 100 configured in the form of a home animation imaging system would provide information that would help patients recover from any procedure and also help guide the patient, in real time, through the recovery process using artificial intelligence to track milestones of the recovery, as well as tracking the progress of the milestones for the recovery in real time in their medical records. Data that may be recorded and analyzed by the patient includes, but is not limited to:
 (a) weight loss;
 (b) weight gain;
 (c) general health at home;
 (d) fat content;
 (e) muscle mass;
 (f) water content.

Such a system may enable standardization of recovery from procedures on a global scale and improve outcomes, quality of care and quality of life. This would also serve avoid the need for costly readmissions and improve documentation of home healthcare.

The home animation imaging system may be used to facilitate personal grooming, including application of facial make-up, other cosmetic applications, dress, etc., in 3D for a number of special events.

Application programming 104 may be configured as a mobile app for use on smartphone or other mobile devices in the form of gaming systems that involve the human body, repair of the human body, and portraying any injury of the human body such as gunshots, stabbings, car crashes, and other trauma that are currently used in gaming systems. Realistic simulations of trauma to the body may be provided, in addition to the ability to repair the trauma. The games could be used to help gamers of all ages that are interested in any medical applications.

Accordingly, Embodiment 2 includes animated simulations from the high definition colorized, photorealism images described in Embodiment 1 above, using the system 100 as applied to standard diagnostic imaging platforms (e.g. in DICOM format).

Following the generation of high definition colorized, photorealism images from the patient's CT/MRI/US scan of the body, or from any standard imaging modality, the original CT/MRI/US scan and the photorealism images may be reviewed. The information for each organ seen on the primitive images of the CT/MRI/US is compared with the images of the patient's body and organs along with personal knowledge of the surgeon and interventionalist of the specific details of the procedure or intervention to be performed. Identification of the actual human anatomy and color from selected black, white and grey features of the CT/MRI/US images, blood vessels, fat, liver parenchyma is preferably performed done by the surgeon and radiologist using the Hounsfield unit scale, standard contrast agents and molecular contrast agents to differentiate densities of blood, water and parenchyma, tumors, scars, etc., are translated into the simulated images by animators in coordination with the photorealism images of the tissues of the selected organs and tissues.

With the guidance of the surgeon and interventionalist, the simulation of the procedure may be developed from actual high definition colorized images of the organs intended for the operation or procedure from the CT/MRI/US scan of the patient's body using the animation platform. Initially, there can be a focus on developing a simulation of one organ, such as the appendix, to simplify the process. Cross-references of the animated simulation being produced with the CT/MRI/US scan may be done on a continuous basis to ensure accuracy of the simulation being produced. Once completed, the animated simulation of the CT/MRI/US scan, or similar modality, will be reviewed and compared with the photorealism rendering by the surgeon, radiologist, interventionalist, etc.

A determination may be made of whether the system is able to reproduce the photorealism images from the DICOM format CT/MRI/US scan without the assistance of the animators and surgeon. The animated simulations may ultimately be reviewed by the entire team, which will ensure accuracy of the automated simulations. Once this is accomplished, a database of animated simulations of all operations and interventions is developed and tested against other patients' CT/MRI/US scans. The animated simulation may be evaluated using practice operation or interventions by the surgeon or interventionalist, respectively, to determine the usefulness of the simulation in helping prepare for the actual operation or intervention.

Once evaluated, the animated simulation may be evaluated again in real-time during the actual operation or intervention using picture-in-a-picture technology to determine the usefulness of the simulation in assisting the surgeon or interventionalist during the actual operation or intervention. The animated simulations may be continuously modified to incorporate artificial intelligence technology and real-time data capture technology to assist the surgeon and interventionalist with the performance and reporting of the details of the operation or intervention. The goal is to ensure safety and improve quality of care by using standard of care protocols that are captured using artificial intelligence as the operation or intervention proceeds in real time. This process may be repeated for other imaging modalities of known patients, such as PET-CT or nuclear medicine scans.

In another example, the same patient's head and body is scanned simultaneously into the system (e.g., using a 4 camera scanning facial recognition technology, as provided by Hydraulx, Inc.). The CT/MRI/US scan is then reviewed in collaboration with the surgeon, radiologist and the animation team and the information transferred into the system (e.g. using NECTAR and Dell computers animation software, such as Poser Pro 2010 3D Modeling & Animation). The information of each organ seen on the primitive images of the CT/MRI/US may be discussed in detail and compared with known images and photographs of the human body and organs from anatomy atlases and detailed information obtained from other documented sources. With the guidance of the surgeon, the images of the organs on the CT/MRI/US scan of the patient's body are then transformed into a high definition photorealism rendering of the internal gastrointestinal organs using the system.

The original CT/MRI/US scan and the photorealism images may be reviewed in collaboration with the surgeon, radiologist, interventionalist and the animation team and the information will be transferred into the animation simulation platform for development of the animated simulation. The information of each organ seen on the primitive images of the CT/MRI/US is discussed in detail and compared with the images of the patient's body and organs along with personal knowledge of the surgeon and interventionalist of the specific details of the procedure or intervention to be performed. Identification of the actual human anatomy and color from selected black, white and grey features of the CT/MRI/US images, blood vessels, fat, liver parenchyma is performed by the surgeon and radiologist using the Hounsfield unit scale, standard contrast agents and molecular contrast agents to differentiate densities of blood, water and parenchyma, tumors, scars, etc., and will be translated into simulated images by the animators in coordination with the photorealism images of the tissues of the selected organs and tissues.

The information and databases, as well as the technology from these processes can also be implemented for home health systems that are connected to electronic medical records, for gaming purposes, for movies and television and for personal grooming programs.

D. General Embodiment 3

As an extension of Embodiment 1, the systems and methods of the present description may be used for functional genomics and molecular imaging to develop "molecular contrasts" for SIMaging.

PET-CT scan imaging currently exists, but the images are of low definition. The quality of definition can be greatly enhanced using the photorealism imaging system 100 of the present description, as well as the ability to image any diseased tissue versus healthy, normal tissue. Similar to that of intravenous and oral contrast agents used in current imaging modalities, the present system would use "molecular contrast" to differentiate different healthy cells and tissues, as well as diseased cells and tissues, from one another using tissue specific-synthetic promoter-driven gene delivery platform to deliver cell and tissue specific imaging genes.

Figure 5:
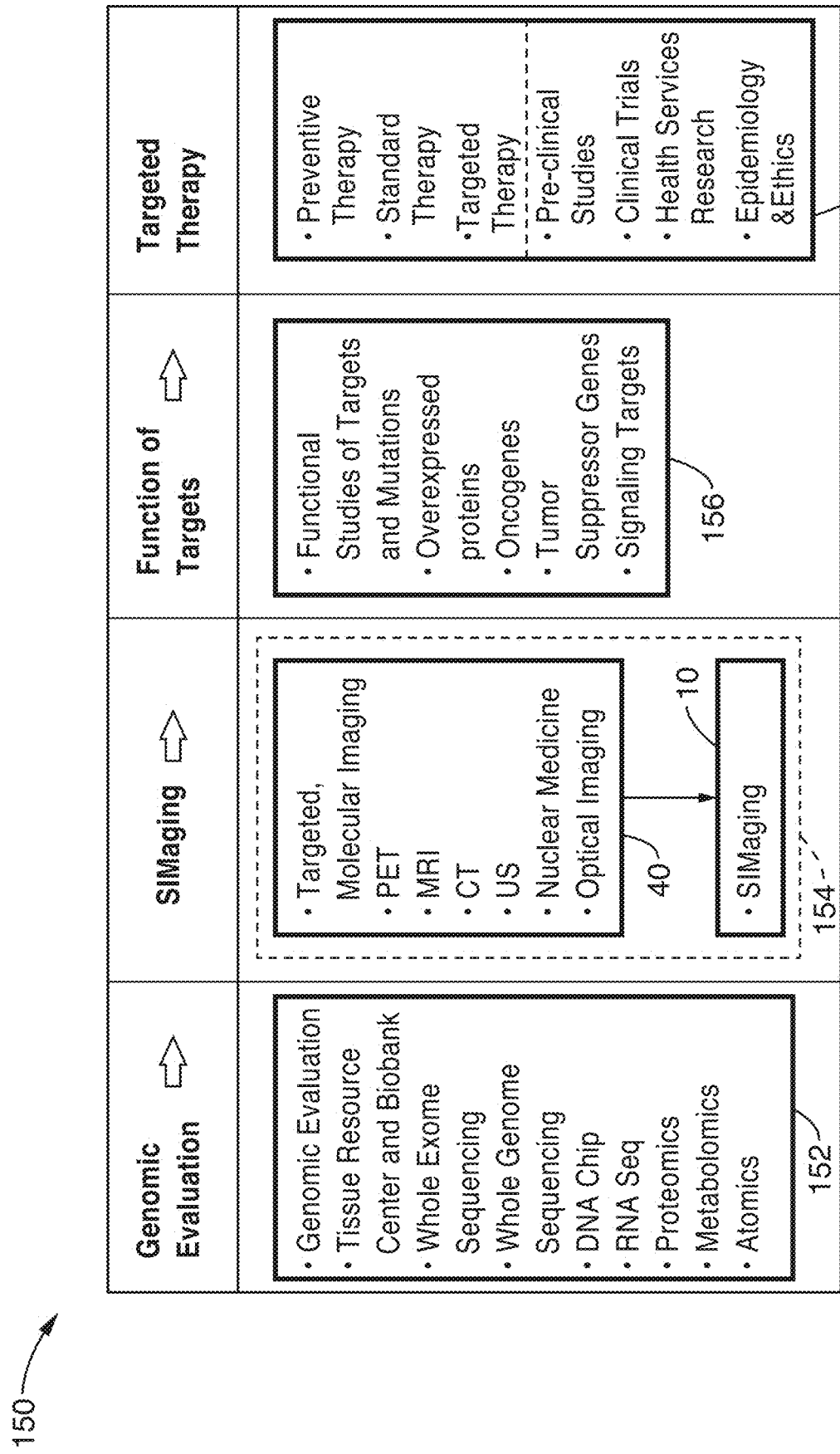
FIG. 5 shows a schematic flow diagram of a model for personalized genomic medicine and surgery according to embodiments of the technology described herein.

FIG. 5 shows a schematic flow diagram of a model 150 for personalized genomic medicine and surgery according to embodiments of the technology described herein. First genomic evaluation is performed at block 152 in the form of one or more of exome or gene sequencing, proteomics, etc. SIMaging method 10 is then performed at block 154 via one or more imaging modalities (e.g. MRI, CT, US, PET, targeted molecular imaging, nuclear medicine, optical imaging, etc.). Functional studies of targets and/or mutations, such as overexpressed proteins, oncogenes, tumor suppressor genes, signaling targets, etc., is then performed at block 156. Finally, targeted therapy (e.g. preventative, standard, and targeted therapies, preclinical studies, clinical trials, etc.) are performed at block 158.

Figure 6:
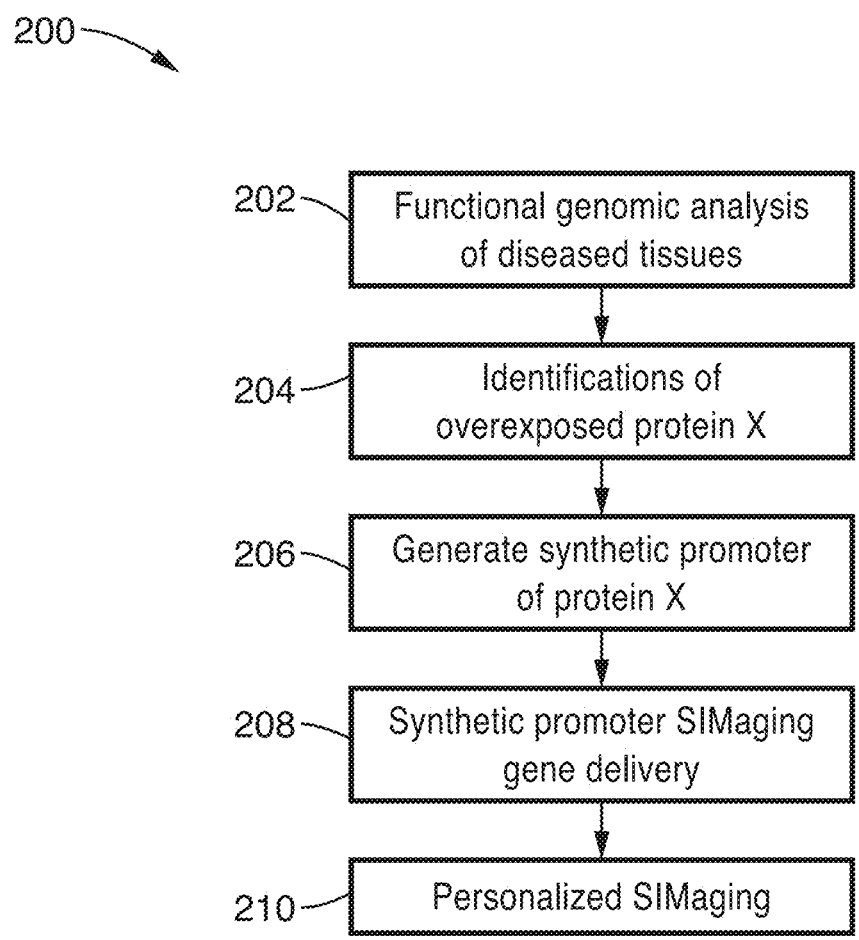
FIG. 6 illustrates a flow diagram of a process flow for enhanced imaging using promoters according to an embodiment of the technology described herein.

FIG. 6 illustrates a flow diagram of a process flow 200 for enhanced imaging using promoters (i.e. molecular contrasts for SIMaging) according to an embodiment of the technology described herein.

The functional genomic analysis system 202 may be performed on all given healthy tissues of the body, as well as diseased tissues for identification of overexpressed Protein X in each given tissue at block 204. This means that that tissue X has the transcriptional mechanisms to cause activation of the promoter of the gene of protein X, thus causing overexpression. For example, the insulin protein is over expressed in healthy islets of Langerans in the pancreas, as well as in insulinoma tumors. Along with others, we have identified that the transcription factor, PDX1, is responsible for activation of the insulin promoter in these healthy and diseased tissues.

At block 206, the synthetic promoter of Protein X is generated, which will drive gene expression in the healthy and diseased tissues. For example, we generated a synthetic insulin promoter (BL promoter) and have shown that the BL promoter is very efficient at tissue specific delivery of imaging genes in islets, insulinoma tumors cells and cancer cells.

Figure 7A:
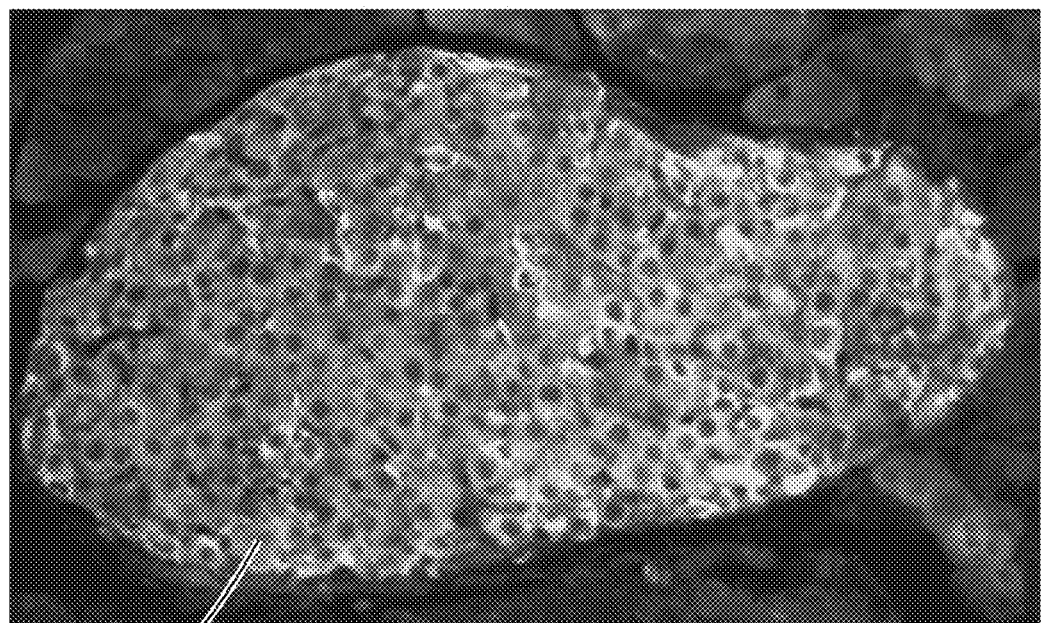
FIG. 7A and FIG. 7B illustrate an embodiment of molecular contrast imaging according to the technology described herein.
Figure 7B:
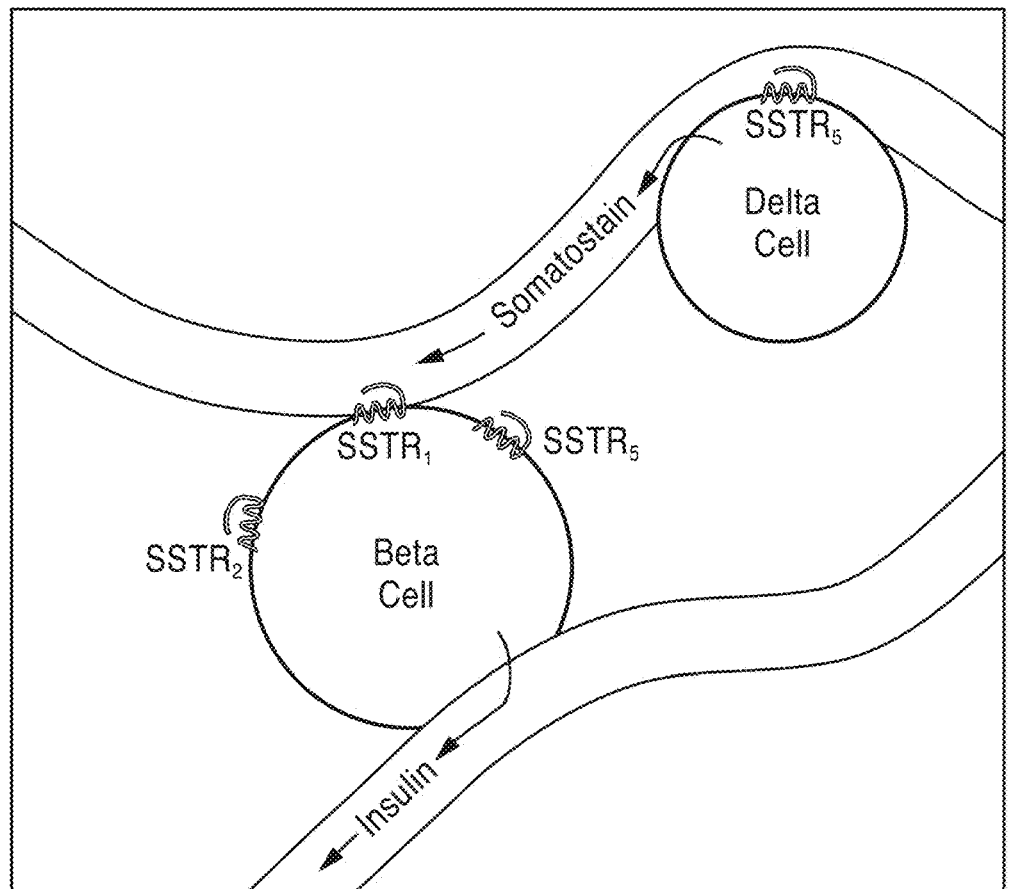

At block 208, SIMaging is performed on the synthetic promoter. The promoter of protein X is used for delivery of theranostic genes, which can be used for enhanced cell and tissue specific imaging of both healthy tissues and diseased tissues, as well as therapy. For example, imaging healthy islets of Langerhans within the pancreas (see image 40c in FIG. 7), as well insulinoma tumors (and other cancers) in mice using the BL promoter may be used to drive thymidine kinase and somatostatin receptor subtype 5 genes. These images can then be used to generated photorealism images (see image 26c in FIG. 7), and ultimately simulations of healthy and diseased tissues for personalized SIMaging step 210 based upon the patients imaging studies. As defined in the GIFT model shown in FIG. 5, this system represents personalized medicine, and thus is termed SIMaging in accordance with the present description.

The following details the basic science behind the embodiment 200 of FIG. 6. It is to be noted that the BL promoter is labeled as SHIP or "Synthetic Human Insulin Promoter" in this section.

1. Using a functional genomics system we have determined that PDX1 is overexpressed in most cancers and can be used as a target to activate the insulin promoter to drive theranostic genes in cancers. PDX1 promotes PDAC via a PDX1 amplifying loop and is a target for insulin promoter driven imaging and therapies.

2. We have demonstrated that delivered Rat Insulin Promoter (RIP)-Thymidine Kinase and an analogue of FHBG successfully imaged human pancreatic cancer tumors in mice in vivo using optical imaging. For translational purposes, we developed and tested a novel synthetic human insulin promoter (SHIP or BL promoter) utilizing PDX1-activation sites of the human insulin promoter (HIP). Preliminary data demonstrates that SHIP (BL) successfully drives CAT reporter gene expression with significantly higher efficiency than RIP, HIP or CMV promoters in PDX1-positive human pancreatic cancer cells (PANC1), but not in PDX1-negative HPDE cells. We delivered iv SHIP-TK nanoparticles which were successfully expressed in human pancreatic cancer tumors in mice and imaged using optical scanning imaging. The study was repeated on insulinoma tumors in mice and the tumors were successfully imaged. This preliminary data demonstrates that systemically delivered SHIP (BL Promoter) drives gene expression in PDX1-positive human pancreatic cancer and insulinoma tumors in mice with great efficiency, demonstrating the feasibility of the imaging studies using "molecular contrasts".

3. We have shown that the novel SHIP (BL promoter) drives chloramphenicol acetyltransferase (CAT) gene expression with significantly higher efficiency than RIP and HIP in human pancreatic cancer cells. To determine whether SHIP-driven gene expression can be determined using bioluminescence imaging and microPET imaging, SHIP-luciferase is first transfected into pancreatic cancer cell lines with varying PDX1 expression levels, including cell lines PANC1 (PDX1-high), MiaPaCa2 (PDX1-medium) and A549 (PDX1-low), as well as benign HEK293 cells with various doses of PDX1 transfections. Bioluminescence imaging is performed at 24, 48 and 72 hours after gene transfection. The same strategy with imaging TK gene expression driven by SHIP is repeated with microPET imaging using 18F-FHBG. After validation of the accuracy of bioluminescence imaging and microPET imaging in cell lines, these in vitro SHIP-luciferase and SHIP-TK imaging experiments are repeated with the presence of bi-shR-NAPDX1 or empty-vector NPs, and followed by bioluminescence imaging or microPET imaging at various time points after bi-shRNAPDX1 treatment, respectively. The responses of PDX1-expressing PDAC cell lines to the bi-shRNAPDX1 NP treatments are analyzed and compared with the control groups.

4. We have shown that the SHIP promoter drives CAT gene expression with significantly higher efficiency than RIP and HIP in PANC1 cells. To determine whether SHIP-driven gene expression can be imaged using bioluminescence or microPET imaging, SHIP-luciferase or SHIP-TK is first transfected into PDAC cell lines with varying PDX1 expression levels and bioluminescence or microPET (with 18F-FHBG) imaging is performed at 24, 48 and 72 hours after gene transfection. Having experience with RIP-TK imaging in PANC1 subq tumors in SCID mice, test the SHIP-driven gene imaging of PDAC is tested in vivo. The xenograft tumor models are created as follows:

i) stably transfected SHIP-TK-PANC1 cells are placed subq in nude mice; stably transfected SHIP-TK-MiaPaCa2 cells are placed subq in nude mice (n=5 each); the tumors are imaged by microCT after day 30, 60, 90 following implantation of the cells. The subq tumors are measured and the size will be correlation to imaging size. Once the parameters are determined, stably transfected SHIP-TK-PANC1 cells are placed orthotopically in nude mice; stably transfected SHIP-TK-MiaPaCa2 cells will be placed orthotopically in nude mice (n–15 each); the tumors are imaged by microCT after day 30, 60, 90 following implantation of the cells. The orthotopic tumors are measured by sacrificing 5 mice at each time point and the size will be correlated to imaging size. Once these parameters are known, then PANC1 or MiaPaCa2 cells are implanted orthotopically in nude mice (n=15 per group) to test systemically delivered SHIP-TK imaging system. When tumors are measured more than 0.5 cm in diameter by microCT, (~30 days after implantation) the mice are given one dose of 35 ug of iv injection of SHIP-TK NP, followed by 18F-FHBG then studied using microPET at 24, 48 and 72 h after injection to determine whether the PDAC tumor can be detected. The background noise of islets is also be determined.

ii) Once these parameters are known, along with the data from aim 2a on PDAC tumor volume in KPC mice, KPC mice (n=10) at the optimal age (e.g., 8-10 weeks) receive 35 ug of SHIP-TK NP via tail vein and are imaged by micro-PET following 18F-FHBG at 24, 48 and 72 hours after injection. The mice are then treated with three biweekly cycles of 35 ug of mouse-bi-shRNAPDX1 NP. Imaging is repeated 2 weeks after each treatment. Tumors are then harvested to compare tumor volumes, as well as TK and PDX131/46 expression levels.

iii) These studies are repeated using SHIP-Luc-PANC1 and SHIP-Luc-MiaPaCa2 nude mice model and imaged using Bioluminescence imaging system to image tumors following same protocols as described above. A comparison of these imaging studies may determine the most sensitive and accurate approach for further studies.

5. Test data demonstrates that systemically delivered rat insulin promoter-lacZ (RIP-lacZ), but not CMV-lacZ, resulted in tumor specific expression of LacZ in PDX1-positive metastatic PANC1 tumors harvested from the peritoneal cavity of SCID mice. Furthermore, systemically delivered RIP-Thymidine Kinase and an analogue of FHBG successfully imaged PANC1 subcutaneous tumors in SCID mouse in vivo using optical imaging. For translational purposes, we developed and tested a novel synthetic human insulin promoter (SHIP) utilizing PDX1-activation sites of the human insulin promoter (HIP). Preliminary data demonstrate that SHIP successfully drives CAT reporter gene expression with significantly higher efficiency than RIP, HIP or CMV promoters in PDX1-positive PANC1 cells, but not in PDX1-negative HPDE cells. We next developed a SHIP driven Luciferase-RFP (SHIP-Luc2RFP) fusion reporter gene assay and generated stably transfected MiaPaCa2-SHIP-Luc2RFP and PANC1-SHIP-Luc2RFP PDAC cell lines, which can be reliably used to visualize PDX1 gene expression and activity in response to bi-shRNAPDX1 therapy in vitro. These cells are used to study PDX1 expression and the mechanisms in aim 1. Having considerable experience with RIP-TK and pro-drug ganciclovir (GCV) therapy in PDAC mouse models, we delivered iv SHIP-TK NPs in a PANC1 xenograft SCID mouse model, which were successfully expressed in PANC1 tumors. When treated with GCV, PDX1-positive PANC1 tumor volume was significantly suppressed with greater efficacy than CMV-TK/GCV or RIP-TK/GCV. These preliminary data demonstrate that systemically delivered SHIP drives gene expression in PDX1-positive PDAC cells and tumors in mice with great efficiency, demonstrating the feasibility of personalized imaging and therapy.

Figure 8A:
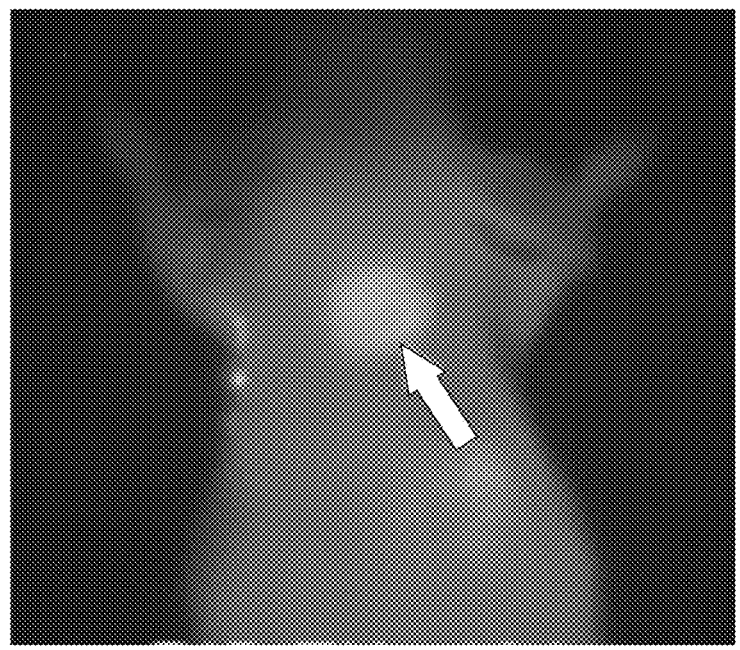
FIG. 8A and FIG. 8B illustrates an example of enhanced imaging of pancreas cancer using promoters according to an embodiment of the technology described herein.
Figure 8B:
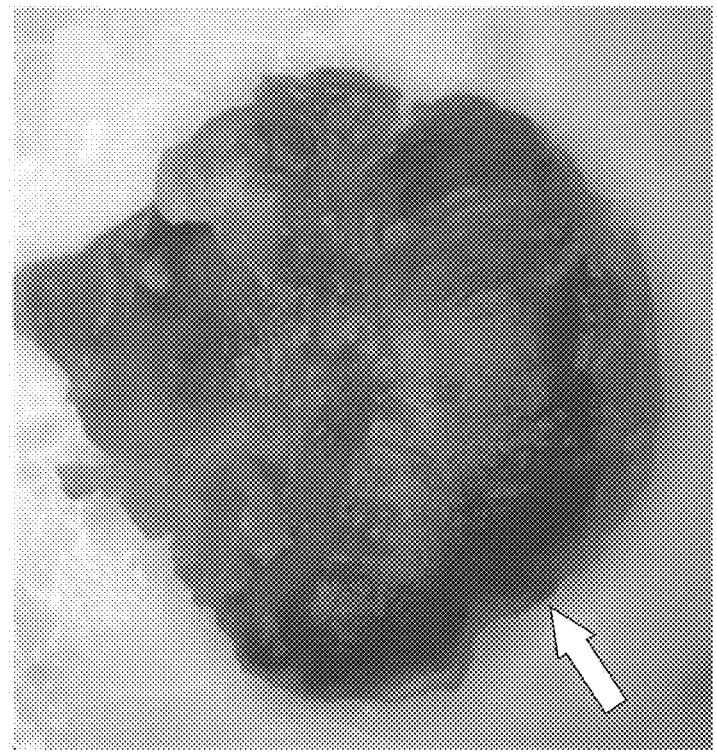

FIG. 8A and FIG. 8B show an In vivo PANC1 tumor-specific imaging using iv RIP-TK/FHBG (FIG. 8A) and RIP-lacZ (FIG. 8B). The image in FIG. 8B is a high definition photorealism of a human pancreatic cancer that was growing in a mouse and was stained blue with a targeted insulin promoter gene delivery system, thus exemplary of SIMaging in accordance with the present description.

Figure 9A:
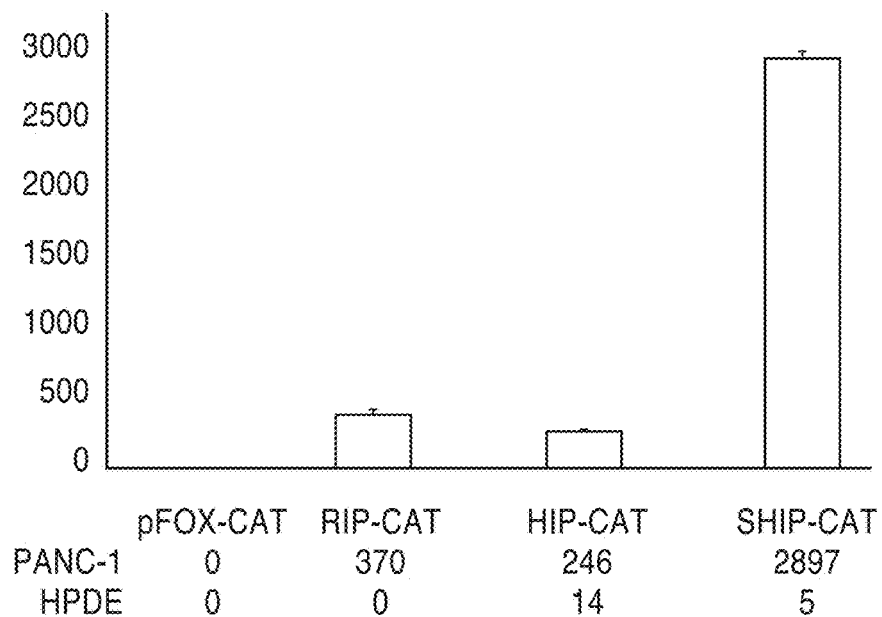
FIG. 9A through FIG. 9D illustrate an example of enhanced imaging of a tumor in mice using promoters according to embodiment of the technology described herein.
Figure 9B:
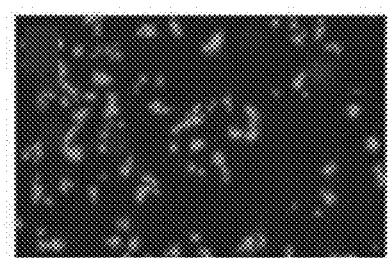
Figure 9C:
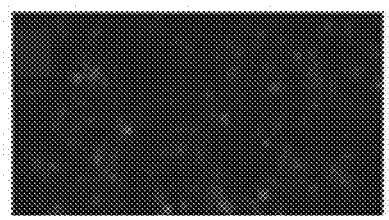
Figure 9D:
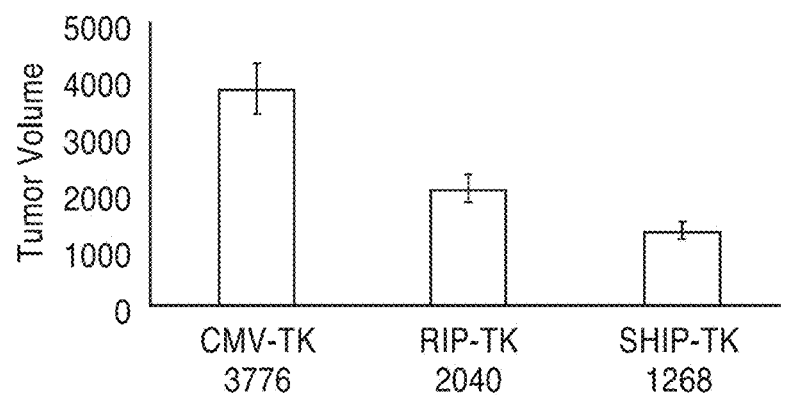

FIG. 9A through FIG. 9D show reporter assay of SHIP (BL) versus RIP and HIP (FIG. 9A). SHIP-Luc2RFP PDAC cell lines before and after PDX1 knocking down and shown in (FIG. 9B and FIG. 9C. FIG. 9D shows SHIP-TK/GCV successfully targeted and suppressed PDX1-positive PANC1 tumor volume in mice.

Accordingly, the technology described herein provides an imaging platform that is capable of producing high definition color visual renderings, essentially "photorealistic-type" images, from the two-dimensional black and white images currently obtained from standard tests, such as CT scans, MRI, ultrasound, brain scans, nuclear medicine scans, PET scans, and other targeted imaging technology. These images can be used alone, or can in turn be used for creating real-time simulations that will assist healthcare professionals of all specialties improve their quality of care for their patients. These real-time simulations, or animations, can further be used for the standardization and/or documentation of that care in real time E. Example Data Extraction A simulation was performed to build a basic pipeline to import raw image scan data from current generation medical imaging devices along with a visualization toolset.

Raw data was acquired from an ACUSON *Sequoia* 512 ultrasound system at somewhat lower resolution (256×256×32 voxels compared to 221×251×143 voxels on a GE E6 system or about 25% of the measurement points. A higher resolution CT scan of an adult male was also provided at a resolution of 256×256×256. A demo rendering program was ported to run on a Linux system along with a full import pipeline to load data into Houdini. This allowed direct comparison of the quality of US data with CT data.

With a basic conversion pipeline, filtering and rendering were performed on the two main data sets: the CT scan from Siemens and the US scan.

The following procedure was used:

First, raw data is imported into Houdini using the custom decoder described above for either the Siemens or GE .vol files. From here we have a standard volume representation that can be processed using a variety of tools.

The following steps were used to produce renderable geometry:

a. Filter the raw volume with a mean value (box) filter.
b. Convert the volume into a level set.
c. Carve out obvious noise and outliers using a spherical volume cutter.
d. Smooth the level set with a Gaussian filter.
e. Convert the level set to polygons (renderable geometry).

From here three slightly different meshes are produced for blending:

a. Regular: the direct result of level set to polygon conversion.
b. Medium geometric smoothing: average neighboring point positions.
c. Aggressive geometric smoothing: average positions within a specific search radius.

The three meshes are blended with weights. The smoothest has the biggest influence, while the regular mesh has the least. The goal is to retain subtle variations in the data while maintaining the smooth shape. The resulting blended mesh is smoothed again at the edges, and finally we apply a "peaking" filter by pulling the mesh a tiny bit inward along the normal direction.

For rendering, Houdini's marble shader was used, which implements physically based subsurface scattering. This mimics the transport of light in semi-translucent materials like skin. Rendering produces several image layers that can be composited together and placed on top of the background.

Once imported, the same processing steps can be applied to any type of volume data to produce images. Although this set of steps requires some manual work, the process is repeatable and can be captured in a procedure within Houdini so that additional images can be produced relatively quickly.

Figure 10A:
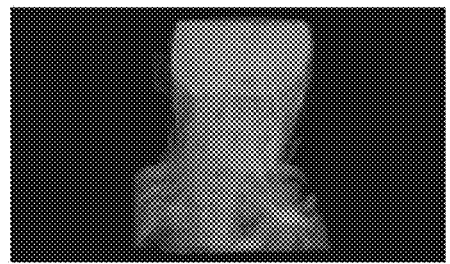
FIG. 10A and FIG. 10B show a raw scan and isosurface render, respectively, using CT data.
Figure 10B:
Figure 10C:
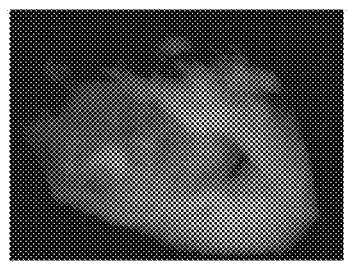
FIG. 10C and FIG. 10D show a raw scan and isosurface render, respectively, for US data.
Figure 10D:

FIG. 10A and FIG. 10B show a raw scan and isosurface render, respectively, using CT data from the Siemens example data sets and FIG. 10C and FIG. 10D show a raw scan and isosurface render, respectively, for the GE US data. These were imported into Houdini using our custom decoder steps detailed above and then processed/rendered using Houdini native tools. Note that these data sets use very different imaging technology (CT versus US), but they are recorded at comparable resolution (albeit with the caveat mentioned above that the CT dataset has a resolution of 256×256×256). With the CT scan you can easily pick out many fine scale details of the subject including skin wrinkles and other fine geometric details. This is without any further processing of the raw volume data. US data seems inherently noisy.

Figure 11A:
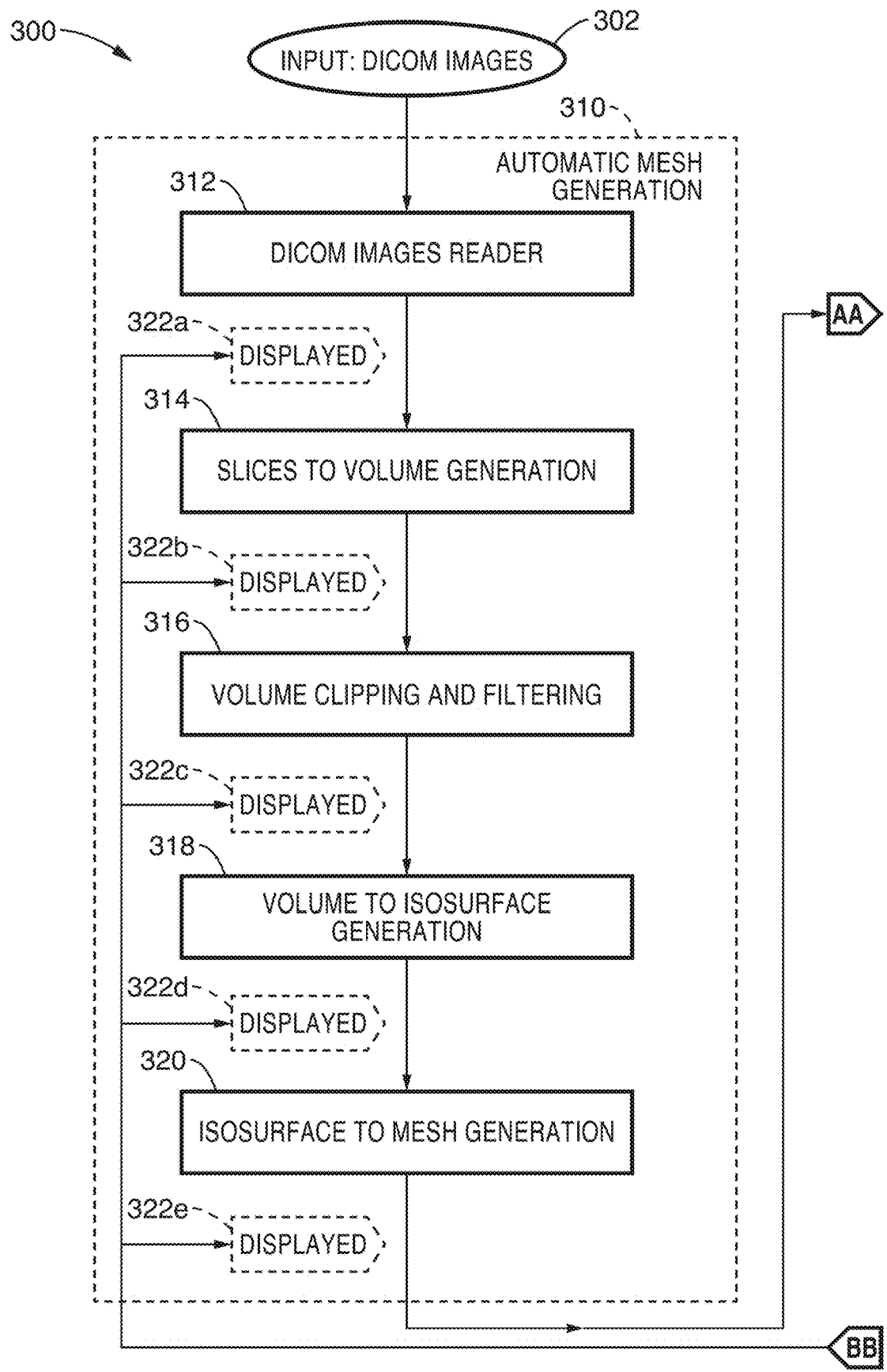
FIG. 11A through FIG. 11C show a flow diagram for a processing method for automatic high-quality rendering of arbitrary human dicom scans with a virtual camera.
Figure 11B:
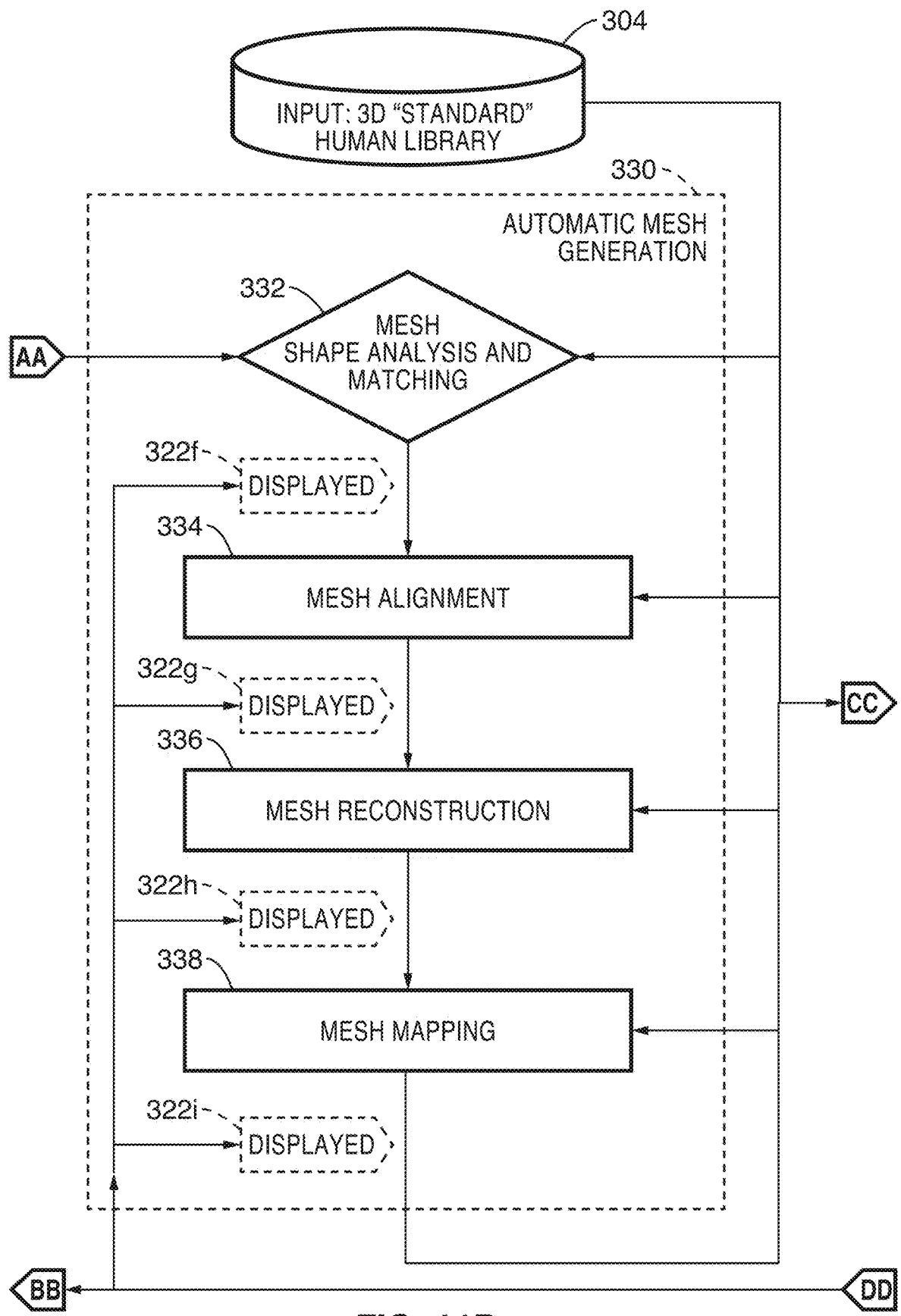
Figure 11C:
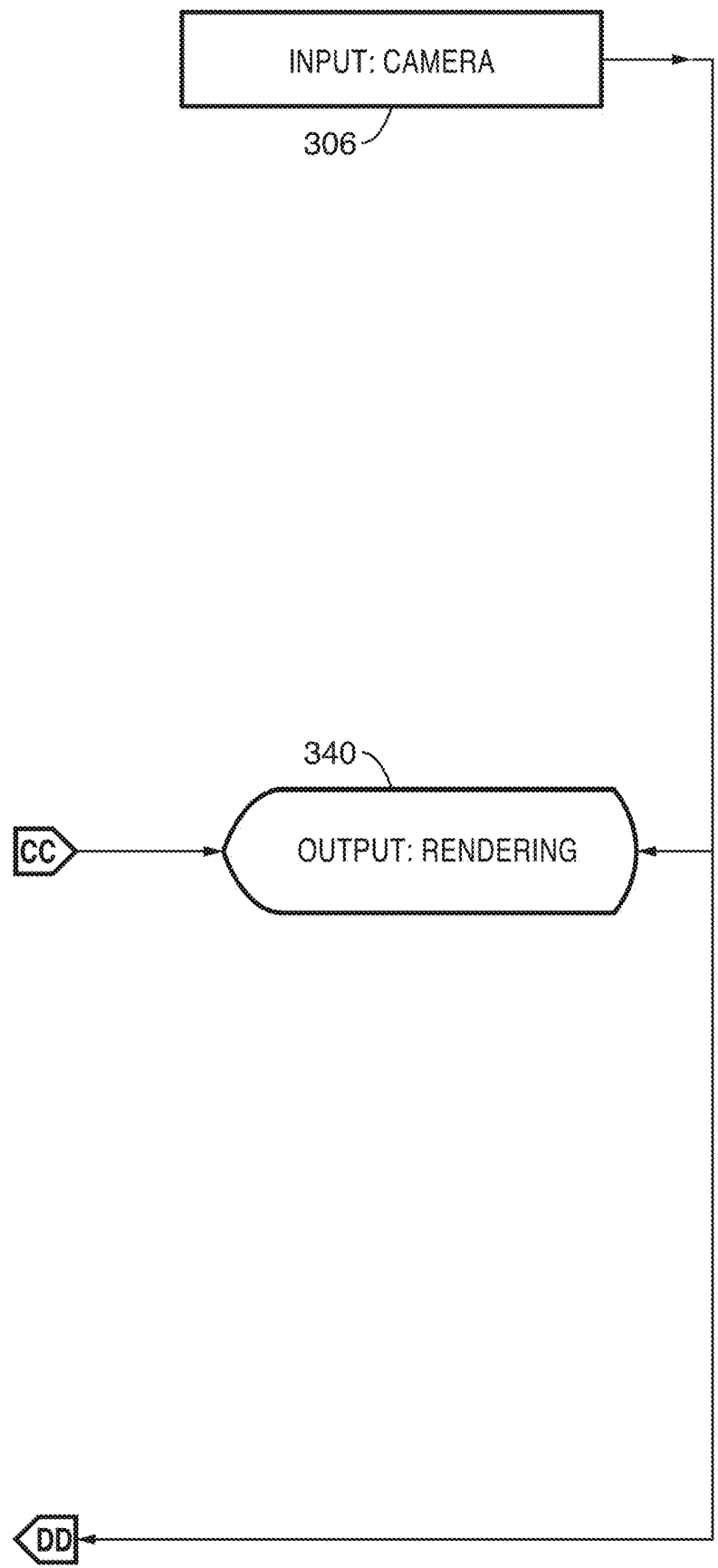

FIG. 11A through FIG. 11C show a flow diagram for a processing method 300 for automatic high-quality rendering of arbitrary human dicom scans with a virtual camera. Method 300 enables input from three separate sources: dicom images 302 (e.g. arbitrary image scans from MRI, CT, etc.), 3D "standard" human library 304 (e.g. complete human body dataset (mesh models, textures, shaders, etc.)), and camera input 306 (arbitrary virtual camera view).

DICOM image data input 302 is fed into the automatic mesh generation module 310, wherein it reads the dicom images and generates the series of slices at first step or node 312. This step allows the user to optionally display the series of slices in the system viewport at 322a (i.e. hardware rendering).

Next at step 314 the series of slices are converted to a volume. This step allows the user to optionally display the generated volume in the system viewport at 322b.

Next at step 316, the volume data is clipped and filtered. Ideally, mean/Gaussian kernels are used for filtering. This step allows the user to optionally display the volume result in the system viewport at 322c.

Next at step 318, the isosurface is generated from the volume. Ideally, OTSU volume histogram thresholds are used to generate the isosurface. This step allows the user to optionally display the generated isosurface in the system viewport at 322d.

Next at step 320, the polygon mesh shape is generated from the volume. This step allows the user to optionally display the generated polygon mesh shape in the system viewport at 322e. This output is then fed into the automatic mesh processing module 330.

At step 332, the generated mesh is analyzed and identified. The generated mesh is morphologically compared against all the ones of the standard human library in order to find its matching, and thus identify it. Heat equation/propagation/laplace-beltrami operator/temperature distribution histograms may be used for the morphological/shape analysis and matching algorithm. This step allows the user to optionally display the matching result in the system viewport at 322f.

At step 334, the generated mesh is aligned (e.g. translated, rotated and scaled in order to fit with its matching). An iterative closed-points algorithm is used for the alignment algorithm. This step allows the user to optionally display the fitting result in the system viewport at 322g.

At step 336, the generated mesh is reconstructed. An iterative closed-points algorithm is used for the reconstruction algorithm. The generated mesh is reconstructed by copying the missing parts from its matching. This step allows the user to optionally display the reconstruction result in system viewport at 322h.

At step 338, the generated mesh is texture mapped by copying the coordinates and assigned textures from its matching. An iterative closed-points algorithm is used for the mapping algorithm. This step allows the user to optionally display the texture mapping result in the system viewport at 322i.

At step 340, the rendering is output. The resulting mesh is software rendered at an arbitrary camera view, an arbitrary resolution, and with a high-quality texturing and shading.

Exemplary software code for carrying out the processing steps of method 300 is found in Appendix A. Appendix A provides an embodiment of instructions contained in application programming 104 may be executable on a processor 106 to perform the functions shown in method 300 of FIG. 11, or any other method described herein.

F. Additional Applications

The animation of a laparoscopic appendectomy will demonstrate that the patient is in the supine position with the left arm tucked. The monitors are positioned at two o'clock and four o'clock and the patient is under general anesthesia. An incision is made in the midline of the umbilicus and the umbilical ring is dilated. A 12-mm blunt trochar is placed into the abdominal cavity which is then insufflated with $CO_2$ gas. Two 5-mm ports are placed under direct camera vision in the left flank. The operation then proceeds in conjunction with the animated CT image of the inflamed appendix as well as the animated simulation that has been developed from patient's CT scan. An exploration is performed which reveals all normal organs within the abdominal cavity except for the inflamed appendix. The adhesions are taken down using blunt and sharp dissection. The base of the appendix is lifted cephalad using a grasper. The mesoappendix is identified. The base of the appendix is then gently dissected using a Kittner dissector. Once a window is obtained between the base of the appendix and the mesoappendix a 12-mm stapler is placed into the abdominal cavity using the umbilical port. A 5-mm camera is used from the 5 mm lateral port. The base of the appendix is then stapled. The meso appendix is identified and stapled using a GIA stapling device with a vascular load. The appendix is then placed into a specimen bag and removed out of the umbilical port. The staple lines are examined. If irrigation is needed, it is performed at this point. The trochars are removed, the gas is removed, and the umbilical trochar site is closed with interrupted sutures of #0 Vicryl. The skin is closed with #4-0 Monocryl. Steri-Strips are applied. Sterile dressings are applied. The patient is awakened and then taken to the recovery room.

The animated simulation in accordance with the present description is used on the screen utilizing picture-in-a-picture technology. The animated simulation of the appendectomy is also used to help guide the surgeon through the operation. The videos of actual laparoscopic appendectomies are linked to CT scans, MRI scans and ultrasounds will be used to develop the animated simulation. This constitutes personalized surgery/interventions based upon the patient's imaging studies and animated imaging. Similar personalized animated simulations can be developed for all operations and interventional procedures.

Personalized imaging using whole body scanning sequentially over time may also be implemented utilizing the systems and methods of the present description. The animated image and simulation methods may be used to create whole body scanning that to follow patients sequentially over time to understand their current health status as well as pathophysiology and the progression of any disease that might be present, such as cancer. Personalized imaging using whole body scanning may also be used to develop home imaging systems to develop weight loss, weight gain, general health conditions at home, and can be connected to an electronic medical record. For example, the patient's differential of muscle and fat versus bone can all be ascertained using a home imaging system using animated imaging.

The systems and methods of the present description may also be implemented for application of personal grooming, including facial make-up, other cosmetic applications, dress, etc in 3D for a number of special events The systems and methods of the present description may also be combined with 3D printing technology to produce models of the patient's body, head, organs, cells for enhanced imaging, diagnoses, therapy and personal uses.

Personalized animated imaging for diagnostics (Embodiment 1) produces a photorealism rendering of the patient's body and organs. An actual color photograph of any diagnostic image transforms diagnostic capability for the radiologist and clinicians of all specialties, as well as education of the patient. The images may be used for real time simulations for practice of a procedure, as well as realtime use during the procedure, for interventionalists of all specialties, including all surgical specialties, radiology, pulmonary, anesthesia, gastroenterology, etc. The images may be used on a daily basis to transform imaging, diagnostic capabilities and therapy in all hospitals and clinics worldwide. The images and animations are transformative for training in all specialties. The images may be used for home health systems to help patients monitor their weight, body mass, body fat content, body water content, body muscle content, which can be connected to an electronic medical record. The system would allow users to visualize and save images of their body images over time.

Personalized animated simulation for any interventional procedures, as provided in Embodiment 2, may be implemented to assist surgeons and interventionalists of all specialties in practice for a given procedure, and also help guide the interventionalist in real time through the procedure using artificial intelligence, like a GPS, and to track milestones of any procedure, as well as tracking the progress of the milestones for the procedure in real time in the medical records. This would allow standardization of procedures on a global scale and improve outcomes and quality of care and improve documentation of all procedures worldwide. This would also avoid the need for costly and inaccurate dictations and improve documentation of healthcare.

The systems and methods of the present description may also be implemented for education for patients, students, medical students, trainees and practicing physicians (CME).

In one embodiment, personalized imaging using whole body scanning may be performed sequentially over time, and may be coupled with artificial intelligence.

In another embodiment, the system may comprise a home animation imaging system to determine weight loss, weight gain, general health at home, fat content, muscle mass, water content, connected to an EMR using artificial intelligence to guide the patients through the process. The home animation imaging system would help patients recover from any procedure and also help guide the patient in real time through the recovery process using artificial intelligence to track milestones of the recovery, as well as tracking the progress of the milestones for the recovery in real time in the medical records. This would lead to standardization of recovery from procedures on a global scale and improve outcomes, quality of care and quality of life. This would also avoid the need for costly readmissions and improve documentation of home healthcare.

The technology of the present description may be implemented to evaluate employees worldwide, including the evaluation of athletes. The technology may be used to evaluate both anatomy and physiology (form and function).

Another implementation of technology is 3D printing to create models of the patients' organs, patients head and torso, and diseases.

The technology may comprise a system configured for personal grooming, including facial make-up, other cosmetic applications, dress, etc., in 3D for any number of special events, such as evening socials, proms, weddings, bar mitzvahs, etc.

Face and body recognition technology may be implemented, with populating the site with internal organs. Medical knowledge may be used to navigate the animated imaging and videos, and be used for movies, television, music videos and internet as well for research purposes in laboratories, clinics, hospitals and medical schools.

SIMaging systems and methods may be used for military, paramedic and hospital emergency room rescues. The system may be incorporated into a portable unit, like an ultrasound configured to take images/photos of the internal organs of an injured soldier or civilian and relay that information back to a MASH unit for guidance based upon the image/photo of the internal injury.

In the hospital, the CT scans and ultrasounds are greatly enhanced using the system of the present description, showing images of the internal organs, thus more clearly defining the injuries of the patient. Artificial intelligence, in the form of a virtual paramedic, may be configured into the system to guide the military medic, paramedic, emergency physician and/or trauma surgeon in the care of the injured soldier or civilian. The actual care can be applied by a robot, which is guided by the virtual paramedic or virtual surgeon. The simulations would also be used for education for all health care providers, guided by the virtual paramedic or virtual surgeon.

Mobile CT, MRI and ultrasound mobile units may be configured to make house calls to patients for imaging and care conveyed back to the electronic medical record of the health system. The actual images and care can be applied by a robot, which is guided by the virtual nurse, virtual paramedic or virtual surgeon and documented in real time. The robot could be a personal avatar that assists with all applications of SIMaging to help with health maintenance for each person.

SIMaging software in accordance with the present description may be used in home portable units, such as ultrasounds, that are safe and easy to use to generate photorealistic images of the internal organs. The actual images can be taken by a robot avatar, which is guided by artificial intelligence in the form of the virtual paramedic or virtual nurse. Therefore, SIMaging software could be part of robotic avatars that are used at home as virtual trainers, valets, lady's maids, paramedics or virtual nurses.

SIMaging software in accordance with the present description may be configured for automatic photographic enhancement, in which the SIMaging software is implemented in a camera to enhance the quality of photograph produced, such as that seen with common manual enhancement of images via "airbrushing" or the like. The photographs can be taken by the person or a robotic avatar, and are guided by the virtual photographic SIMaging software.

SIMaging software configured for personal grooming software may include tutorials on diets, weight loss, weight gain, exercise programs, attire, facial make-up, other cosmetic applications, etc., in 3D high definition. This may include artificial intelligence, in the form of a virtual valet or lady's maid or personal avatar, to help the viewer with tutorials on the basic principles of how to eat, exercise, to dress and how to apply make-up to optimize one's health and image. The SIMaging personal grooming software may incorporate how the world's experts in diet, exercise, fashion design and make-up apply their craft for any given event world wide to advise the viewer on how to prepare, dress and apply their make-up for any number of special events, such as vacations, evening socials, red carpet events, balls, proms, weddings, bar mitzvahs, funerals, on a world wide basis. The make-up can be applied by a robotic avatar, which is guided by SIMaging software. The software will include how the stars of all entertainment fields dress and apply for make-up for any given social event on a global basis.

An interested viewer may use SIMaging personal grooming software to learn how to dress and apply make-up on their own high definition images using artificial intelligence, as a virtual valet or virtual lady's maid or personal avatar, to take them through the basics of make-up application. The viewer will get to see how they look with different styles of clothing. The viewer will get to see how they appear with each different application of eye liner, powder, facial liners, rouge, lipstick, eyebrow enhancement or trimming, wigs, false eyelashes, skin color, tanning, etc. The make-up can be applied by a robotic avatar, which is guided by SIMaging software.

The SIMaging personal grooming software may be used for educational and training purposes in beauty and design schools and acting schools worldwide, guided by the virtual valet or lady's maid or personal avatar.

The SIMaging personal grooming software may be used by entertainers of all types, producers, directors, dress designers worldwide to help them prepare for any given entertainment event, such as movies, television, stage, ballet, shows, concerts, sporting events, etc., all guided by the virtual valet or lady's maid or personal avatar. The software will demonstrate their images, or images of a given performer or athlete, in 3D high definition, in any given attire and make-up in helping to prepare for any given entertainment event. For example, producers, directors and casting agents will use this software to help select the most appropriate actor or actress for a role in a proposed movie or television show, as well as help the actor or actress prepare for that movie or show. The make-up can be applied by a robotic avatar, which is guided by the SIMaging software.

The SIMaging personal grooming software may assist in teaching the basics of how exercise and diet will help them to gain or lose weight and how fit they will appear with selected exercise regimens, all guided by the virtual trainer, virtual valet or virtual lady's maid or personal avatar, which is guided by SIMaging software.

Once the basics are learned, the viewer may use the software and artificial intelligence, in the form of the virtual valet or virtual lady's maid or personal avatar, to help prepare for any given social event on a worldwide basis. For example, if the person attends a wedding in China, the SIMaging software may help them prepare the appropriate style of dress and make-up for such an event and allow how they will appear for that event. The make-up can be applied by a robotic avatar, which is guided by SIMaging software. The software will help them keep track of their own clothing and what might be needed for any given event, as well as what clothes and make-up that were chosen for any previous event. The SIMaging software and artificial intelligence, in the form of the virtual valet or virtual lady's maid or personal avatar, will give advice as to what the world fashion designers and make-up artists would choose for any given event and how the stars might appear for that event or for any previous event. The clothing can be retrieved from the closet by a robot, which is guided by the virtual valet or virtual lady's maid or personal avatar.

The SIMaging personal grooming software may be configured to demonstrate in 3D high definition how the viewer will appear if they chose an exercise routine and diet for any given event, all guided by the virtual trainer, virtual valet or lady's maid or personal avatar. For example, if the person were planning a beach vacation, the SIMaging software will show the viewer in high definition how their body will look if they were to lose five or ten pounds on a given diet as well as an exercise routine. Routines and diets of leading experts and trainers, as well as predicted results, will be part of the software.

The SIMaging personal grooming software may be used by healthcare providers of all specialties for educational purposes to show patients how they would appear after any body altering therapy, such as plastic surgery, morbid obesity surgery, any operation on the outer body, as well as after chemotherapy, steroids, all guided by the virtual professor, virtual doctor, virtual valet, virtual lady's maid or personal avatar. The software may be used to educate patients on how they and their internal organs will appear with harmful behavioral habits, such as smoking and other illicit drug use, as well as over eating or under eating. The software can also be used to educate patients on how they and their internal organs will deteriorate due to the process of any given disease and how therapies might alter the deterioration of appearance.

The SIMaging personal grooming software may be used by the individual and/or healthcare providers of all specialties for educational purposes to show the viewer how they and their internal body composition will age over time, all guided by the virtual doctor, virtual valet, virtual lady's maid or personal avatar.

The SIMaging personal grooming software may be used by governments, national security agencies, military agencies, and police forces of all specialties for educational purposes to demonstrate how their personnel will appear after training, make-up, dress, or any body altering procedures for the purposes of national security, all guided by artificial intelligence in the form of the virtual tutor, virtual valet, lady's maid or personal avatar. The make-up can be applied by a robot avatar, which is guided by the SIMaging software.

Conversely, the SIMaging personal grooming software may be used by governments, national security agencies, military agencies and police forces of all specialties for identification purposes to demonstrate how any criminal might appear after make-up, dress, or any body altering procedures for the purposes of national security, all guided by artificial intelligence in the form of the virtual agent, virtual tutor, virtual professor, virtual valet, lady's maid or personal avatar.

The SIMaging software may be configured in the form of computer games that assist in learning/practicing medical and surgical interventions, to practice interventions/operations in real time on actual patient images.

The SIMaging software may be configured in the form of home health systems connected to electronic medical records.

The SIMaging software may be configured for real time simulations that could be used for practice of any intervention/operation, as well as realtime use during the procedure, for interventionalists of all specialties, including all surgical specialties, gastroenterology, radiology, pulmonary, anesthesia, pain medicine, cardiology, etc.

The SIMaging software may be coupled with artificial intelligence to guide the surgeon/interventionalist through procedures, like a GPS system, in real time, while documenting each step of the procedure according to standard operating protocols, thus standardizing and documenting procedures and entering the information into databases.

The systems and methods of the present description improve quality of care, improve documentation and lower costs of complications, readmissions and documentation.

The SIMaging software may be configured as home health systems that would help patients monitor their weight, body mass, body fat content, body water content, body muscle content, which can be connected to an electronic medical record.

The images generated by SIMaging software may be used for entertainment purposes; examples would be (a) to produce an animated photograph or movie of a baby in utero for parents expecting their developing baby; (b) to develop medical video games using simulations and for movies.

The SIMaging software may be configured as a home animation imaging system to determine weight loss, weight gain, general health at home, fat content, muscle mass, water content, connected to an EMR using artificial intelligence to guide the patients through the process.

The SIMaging software may be configured as a home animation imaging system to help patients recover from any procedure and also help guide the patient in real time through the recovery process using artificial intelligence to track milestones of the recovery, as well as tracking the progress of the milestones for the recovery in real time in the medical records.

The SIMaging software may be configured as gaming systems that involve the human body, repair of the human body, and portraying any injury of the human body such as gunshots, stabbings, car crashes, and other trauma that are currently used in gaming systems.

The SIMaging software may be configured to create realistic simulations of trauma to the body and provide the ability to repair the trauma.

The SIMaging software may be configured to use of to use artificial intelligence in the form of personal avatars, virtual doctors, virtual surgeons, virtual professors, virtual paramedic, virtual valet, virtual lady's maid, etc. to guide the viewer through the simulation, and the use of robots, which will actually implement the numerous applications. For example, personalized robotic avatars will actually perform the home healthcare, operations, procedures, trauma rescues in the field, make-up application, clothing, photography, etc. for all SIMaging applications, guided by the artificial intelligence built into the software. The robots can also be guided by the doctors or paramedics in real time. Each person could have their own personal avatar, either virtual or an actual robot, which helps guide them through their own health maintenance or personal grooming using SIMaging software.

Embodiments of the technology of this disclosure may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the technology described herein can be embodied in various ways, including but not limited to the following:

1. A computer implemented method for enhanced imaging, the method comprising: (a) transforming a non-color, non-photorealistic image into a high definition colorized photorealistic image; (b) wherein said method is performed by executing programming on at least one computer processor, said programming residing on a non-transitory medium readable by the computer processor.

2. A computer implemented method for enhanced imaging, the method comprising: (a) transforming a non-color, two-dimensional image generated from a diagnostic imaging device into high definition colorized, photorealistic image; (b) wherein said method is performed by executing programming on at least one computer processor, said programming residing on a non-transitory medium readable by the computer processor.

3. The method of any preceding embodiment, further comprising creating animated simulations based on a plurality of said photorealistic images.

4. The method of claim any preceding embodiment, further comprising highlighting an area of interest in the photorealistic image using a molecular contrast promoter.

5. The method of any preceding embodiment, further comprising automatically generating a diagnosis by evaluating characteristics of the areas of interest in the photorealistic image.

6. The method of any preceding embodiment, further comprising: using functional genomics and molecular imaging to generate a molecular contrast; using the molecular contrast to highlight the area of interest.

7. The method of any preceding embodiment, further comprising, further comprising automatically generating a diagnosis by evaluating characteristics of the areas of interest in the photorealistic image.

8. A computer implemented method for creating an animated simulation, the method comprising: (a) transforming a plurality of images of a biological component, feature, characteristic, assembly, or structure, or a combination thereof, into high definition colorized photorealistic images; and (b) assembling said photorealistic images into an animated simulation; (c) wherein said method is performed by executing programming on at least one computer processor, said programming residing on a non-transitory medium readable by the computer processor.

9. An apparatus for enhanced imaging, the apparatus comprising: (a) a computer processor; and (b) programming in a non-transitory computer readable medium and executable on the computer processor for transforming a non-color, non-photorealistic image into a high definition colorized photorealistic image.

10. An apparatus for enhanced imaging, the apparatus comprising: (a) a computer processor; and (b) programming in a non-transitory computer readable medium and executable on the computer processor for transforming a non-color, two-dimensional image generated from a diagnostic imaging device into high definition colorized, photorealistic image.

11. The apparatus of any preceding embodiment, wherein said programming is configured to create animated simulations based on a plurality of said photorealistic images.

12. The apparatus of any preceding embodiment, wherein said programming is configured to highlight an area of interest in the photorealistic image using a molecular contrast promoter.

13. The apparatus of any preceding embodiment, wherein said programming is configured for automatically generating a diagnosis by evaluating characteristics of the areas of interest in the photorealistic image.

14. The apparatus of any preceding embodiment, wherein said programming is configured for performing steps comprising: using functional genomics and molecular imaging to generate a molecular contrast; and using the molecular contrast to highlight the area of interest.

15. The apparatus of any preceding embodiment, wherein said programming is configured for automatically generating a diagnosis by evaluating characteristics of the areas of interest in the photorealistic image.

16. An apparatus for creating an animated simulation, the apparatus comprising: (a) a computer processor; and (b) programming in a non-transitory computer readable medium and executable on the computer processor for: (i) transforming a plurality of images of a biological component, feature, characteristic, assembly, or structure, or a combination thereof, into high definition colorized photorealistic images; and (ii) assembling said photorealistic images into an animated simulation.

17. An enhanced image, comprising: (a) a high definition colorized photorealistic image transformed from a non-color, non-photorealistic image; (b) wherein image transformation is performed by executing programming on at least one computer processor, said programming residing on a non-transitory medium readable by the computer processor.

18. An enhanced image, comprising: (a) a high definition colorized photorealistic image transformed from a non-color, two-dimensional image generated from a diagnostic imaging device; (b) wherein image transformation is performed by executing programming on at least one computer processor, said programming residing on a non-transitory medium readable by the computer processor.

19. A animated simulation, comprising: (a) an assembly of a high definition colorized photorealistic images transformed from non-color, non-photorealistic images; (b) wherein image transformation and assembly is performed by executing programming on at least one computer processor, said programming residing on a non-transitory medium readable by the computer processor.

20. A animated simulation, comprising: (a) an assembly of a high definition colorized photorealistic images transformed from a non-color, two-dimensional image generated from a diagnostic imaging device; (b) wherein image transformation and assembly is performed by executing programming on at least one computer processor, said programming residing on a non-transitory medium readable by the computer processor.

21. An apparatus for enhanced imaging, the apparatus comprising: (a) a computer processor; and (b) a non-transitory computer-readable memory storing instructions executable by the computer processor; (c) wherein said instructions, when executed by the computer processor, perform steps comprising: (i) generating a database of parametric anatomy comprising one or more of volume data and isometric surface models of one or more aspects of the anatomy; (ii) tagging one or more objects within the parametric anatomy; (iii) inputting patient data comprising an imaging scan of a target patient anatomy of a patient; (iv) configuring a base parametric model of patient anatomy as a function of input patient data comprising one or more physical characteristics of the patient; (v) applying data relating to the imaging scan to the base parametric model; (vi) searching the data relating to the imaging scan for one or more markers within the data; (vii) aligning the parametric model to the one or more markers of the imaging scan; and (viii) rendering the aligned parametrical model and imaging scan for photo-realistic display of the patient target anatomy.

22. The apparatus of any preceding embodiment, wherein data relating to the imaging scan comprises DICOM data from one or more of an MRI, CT, or ultrasound scan of the patient.

23. The apparatus of any preceding embodiment, wherein the database is generated by acquiring input from patient data comprising one or more of patient scans, statistics or photos relating to patient.

24. The apparatus of any preceding embodiment, wherein the isometric surface models are configured for photo-real real-time VR rendering.

25. The apparatus of any preceding embodiment, wherein the tagged data is configured so that that can be turned on or off for viewing.

26. The apparatus of any preceding embodiment, the instructions further comprising: allowing manual input for selecting the one or more markers.

27. The apparatus of any preceding embodiment, wherein aligning the parametric model to the one or more markers of the imaging scan comprises isometric surface alignment of the parametric anatomical geometry to the patient's DICOM scan data.

28. The apparatus of any preceding embodiment, wherein the alignment is done taking into account input patient data relating to one or more of weight, height, BMI, X-ray, and patient photos.

29. The apparatus of any preceding embodiment, wherein the alignment is performed on both volume data and isometric surfaces.

30. The apparatus of any preceding embodiment, wherein the alignment is adjusted by manual input via selecting one or more structures on slices of the MRI or CT scan to fine-tune the base parametric model.

31. The apparatus of any preceding embodiment, the instructions further configured for: applying photographic reference of skin color to the output parametric model.

32. The apparatus of any preceding embodiment, the instructions further configured for: auto-alignment and projection of one or more of the following to the parametric model: patient wounds, surgeon markups, X-rays, notes and other text files.

33. A computer implemented method for enhanced imaging, the method comprising: generating a database of parametric anatomy comprising one or more of volume data and isometric surface models of one or more aspects of the anatomy; tagging one or more objects within the parametric anatomy; inputting patient data comprising an imaging scan of a target patient anatomy of a patient; configuring a base parametric model of patient anatomy as a function of input patient data comprising one or more physical characteristics of the patient; applying data relating to the imaging scan to the base parametric model; searching the data relating to the imaging scan for one or more markers within the data; aligning the parametric model to the one or more markers of the imaging scan; and rendering the aligned parametrical model and imaging scan for photo-realistic display of the patient target anatomy.

34. The method of any preceding embodiment, wherein data relating to the imaging scan comprises DICOM data from one or more of an MRI, CT, or ultrasound scan of the patient.

35. The method of any preceding embodiment, wherein the database is generated by acquiring input from patient data comprising one or more of patient scans, statistics or photos relating to patient.

36. The method of any preceding embodiment, wherein the isometric surface models are configured for photo-real real-time VR rendering.

37. The method of any preceding embodiment, wherein the tagged data is configured so that that can be turned on or off for viewing.

38. The method of any preceding embodiment the method further comprising: allowing manual input for selecting the one or more markers.

39. The method of any preceding embodiment, wherein aligning the parametric model to the one or more markers of the imaging scan comprises isometric surface alignment of the parametric anatomical geometry to the patient's DICOM scan data.

40. The method of any preceding embodiment, wherein the alignment is done taking into account input patient data relating to one or more of weight, height, BMI, X-ray, and patient photos.

41. The method of any preceding embodiment, wherein the alignment is performed on both volume data and isometric surfaces.

42. The method of any preceding embodiment, wherein the alignment is adjusted by manual input via selecting one or more structures on slices of the MRI or CT scan to fine-tune the base parametric model.

43. The method of any preceding embodiment, the method further comprising: applying photographic reference of skin color to the output parametric model.

44. The method of any preceding embodiment, the method further comprising: auto-alignment and projection of one or more of the following to the parametric model: patient wounds, surgeon markups, X-rays, notes and other text files.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for enhanced medical imaging, the apparatus comprising:
   (a) a computer processor; and
   (b) a non-transitory computer-readable memory storing instructions executable by the computer processor;
   (c) wherein said instructions, when executed by the computer processor, perform steps comprising:
      (i) generating a database of parametric anatomy comprising one or more of volume data and isometric surface models of one or more aspects of the anatomy;
      (ii) tagging one or more objects within the parametric anatomy;
      (iii) inputting patient data comprising an imaging scan, which comprises a two dimensional black and white imaging scan, of a target patient anatomy of a patient and generating slices which are converted into a volume, then clipping and filtering the volume data, from which an isosurface is generated using an OTSU volume histogram threshold, after which a mesh polygon shape is generated from the isosurface;

(iv) configuring a base parametric model of patient anatomy as a function of input patient data comprising one or more physical characteristics of the patient;

(v) applying data relating to the imaging scan to the base parametric model, to which are applied high resolution textures for photo-realistic quality;

(vi) searching the data relating to the imaging scan for one or more markers within the data;

(vii) aligning the parametric model to the one or more markers of the imaging scan; and (viii) rendering the aligned parametrical model and imaging scan into a colorized 3D photo-realistic display of the patient target anatomy.

2. The apparatus of claim 1, wherein data relating to the imaging scan comprises DICOM data from one or more of an MRI, CT, or ultrasound scan of the patient.

3. The apparatus of claim 1, wherein the database is generated by acquiring input from patient data comprising one or more of patient scans, statistics or photos relating to patient.

4. The apparatus of claim 1, wherein the isometric surface models are configured for photo-realistic real-time VR rendering.

5. The apparatus of claim 1, wherein the tagged data is configured so that it can be turned on or off for viewing.

6. The apparatus of claim 1, the instructions further comprising:

allowing manual input for selecting the one or more markers.

7. The apparatus of claim 2, wherein aligning the parametric model to the one or more markers of the imaging scan comprises isometric surface alignment of the parametric anatomical geometry to the patient's DICOM scan data.

8. The apparatus of claim 7, wherein the alignment is done taking into account input patient data relating to one or more of weight, height, BMI, X-ray, and patient photos.

9. The apparatus of claim 7, wherein the alignment is performed on both volume data and isometric surfaces.

10. The apparatus of claim 9, wherein the alignment is adjusted by manual input via selecting one or more structures on slices of the MRI or CT scan to fine-tune the base parametric model.

11. The apparatus of claim 1, the instructions further configured for:

applying photographic reference of skin color to the output parametric model.

12. The apparatus of claim 1, the instructions further configured for:

auto-alignment and projection of one or more of the following to the parametric model: patient wounds, surgeon markups, X-rays, notes and other text files.

13. A computer implemented method for enhanced medical imaging, the method comprising:

generating a database of parametric anatomy comprising one or more of volume data and isometric surface models of one or more aspects of the anatomy;

tagging one or more objects within the parametric anatomy;

inputting patient data comprising an imaging scan, which comprises a two dimensional black and white imaging scan, of a target patient anatomy of a patient and generating slices which are converted into a volume, then clipping and filtering the volume data, from which an isosurface is generated using an OTSU volume histogram threshold, after which a mesh polygon shape is generated from the isosurface;

configuring a base parametric model of patient anatomy as a function of input patient data comprising one or more physical characteristics of the patient;

applying data relating to the imaging scan to the base parametric model, to which are applied high resolution textures for photo-realistic quality;

searching the data relating to the imaging scan for one or more markers within the data;

aligning the parametric model to the one or more markers of the imaging scan; and rendering the aligned parametrical model and imaging scan into a colorized 3D photo-realistic display of the patient target anatomy.

14. The method of claim 13, wherein data relating to the imaging scan comprises DICOM data from one or more of an MRI, CT, or ultrasound scan of the patient.

15. The method of claim 13, wherein the database is generated by acquiring input from patient data comprising one or more of patient scans, statistics or photos relating to patient.

16. The method of claim 13, wherein the isometric surface models are configured for photo-realistic real-time VR rendering.

17. The method of claim 13, wherein the tagged data is configured so that it can be turned on or off for viewing.

18. The method of claim 13, the method further comprising:

allowing manual input for selecting the one or more markers.

19. The method of claim 14, wherein aligning the parametric model to the one or more markers of the imaging scan comprises isometric surface alignment of the parametric anatomical geometry to the patient's DICOM scan data.

20. The method of claim 19, wherein the alignment is done taking into account input patient data relating to one or more of weight, height, BMI, X-ray, and patient photos.

21. The method of claim 19, wherein the alignment is performed on both volume data and isometric surfaces.

22. The method of claim 21, wherein the alignment is adjusted by manual input via selecting one or more structures on slices of the MRI or CT scan to fine-tune the base parametric model.

23. The method of claim 13, the method further comprising:

applying photographic reference of skin color to the output parametric model.

24. The method of claim 13, the method further comprising:

auto-alignment and projection of one or more of the following to the parametric model: patient wounds, surgeon markups, X-rays, notes and other text files.

* * * * *